(12) United States Patent
Pung et al.

(10) Patent No.: US 10,806,610 B2
(45) Date of Patent: Oct. 20, 2020

(54) STENT

(71) Applicant: MicroVention, Inc., Aliso Viejo, CA (US)

(72) Inventors: Ponaka Pung, Signal Hill, CA (US); Helen Nguyen, Carson, CA (US); Tai D. Tieu, Fountain Valley, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 186 days.

(21) Appl. No.: 16/025,942

(22) Filed: Jul. 2, 2018

(65) Prior Publication Data

US 2018/0311056 A1 Nov. 1, 2018

Related U.S. Application Data

(63) Continuation of application No. 14/994,024, filed on Jan. 12, 2016, now Pat. No. 10,039,655.

(60) Provisional application No. 62/102,483, filed on Jan. 12, 2015, provisional application No. 62/108,699, filed on Jan. 28, 2015.

(51) Int. Cl.
| | |
|---|---|
| *A61F 2/88* | (2006.01) |
| *A61F 2/90* | (2013.01) |
| *A61F 2/954* | (2013.01) |
| *A61F 2/82* | (2013.01) |
| *A61F 2/86* | (2013.01) |
| *A61F 2/852* | (2013.01) |

(52) U.S. Cl.
CPC ............. *A61F 2/885* (2013.01); *A61F 2/90* (2013.01); *A61F 2/82* (2013.01); *A61F 2/852* (2013.01); *A61F 2/86* (2013.01); *A61F 2/88* (2013.01); *A61F 2/954* (2013.01); *A61F 2002/823* (2013.01); *A61F 2250/006* (2013.01); *A61F 2250/0023* (2013.01); *A61F 2250/0036* (2013.01)

(58) Field of Classification Search
CPC .... A61F 2/82; A61F 2/852; A61F 2/86; A61F 2/88; A61F 2/885; A61F 2/90; A61F 2002/823; A61F 2250/0023; A61F 2250/0036

See application file for complete search history.

(56) References Cited

U.S. PATENT DOCUMENTS

| | | | | |
|---|---|---|---|---|
| 5,882,335 | A | 3/1999 | Leone et al. | |
| 6,156,064 | A * | 12/2000 | Chouinard | A61F 2/07 623/1.44 |
| 6,161,399 | A * | 12/2000 | Jayaraman | D04B 1/14 623/1.5 |
| 6,652,570 | B2 * | 11/2003 | Smith | A61F 2/07 623/1.13 |

(Continued)

OTHER PUBLICATIONS

WIPO, U.S. International Search Authority, International Search Report and Written Opinion dated Mar. 13, 2016 in International Patent Application No. PCT/US2016/013102, 8 pages.

*Primary Examiner* — Robert A Lynch
(74) *Attorney, Agent, or Firm* — Inskeep IP Group, Inc.

(57) ABSTRACT

A stent with varying porosity is described. The stent can be comprised of multiple stents attached together. A braided stent may have selected regions of increased thickness. The stent may be comprised of wires that are welded together at their ends in order to minimize vessel trauma. The stent may comprise a helically wound radiopaque wire wound through the stent.

22 Claims, 31 Drawing Sheets

(56) References Cited

U.S. PATENT DOCUMENTS

| | | |
|---|---|---|
| 2007/0250154 A1 | 10/2007 | Greenberg et al. |
| 2008/0221658 A1* | 9/2008 | Martin .................... A61F 2/885 623/1.12 |
| 2009/0177268 A1 | 7/2009 | Lundkvist et al. |
| 2010/0274346 A1 | 10/2010 | Chouinard et al. |
| 2011/0071613 A1 | 3/2011 | Wood et al. |
| 2011/0144739 A1 | 6/2011 | Cattaneo |
| 2013/0166010 A1 | 6/2013 | Vad |
| 2013/0190676 A1* | 7/2013 | Dickinson ............... A61F 2/064 604/8 |
| 2013/0245745 A1 | 9/2013 | Vong et al. |
| 2015/0045874 A1 | 2/2015 | McMahon et al. |

\* cited by examiner

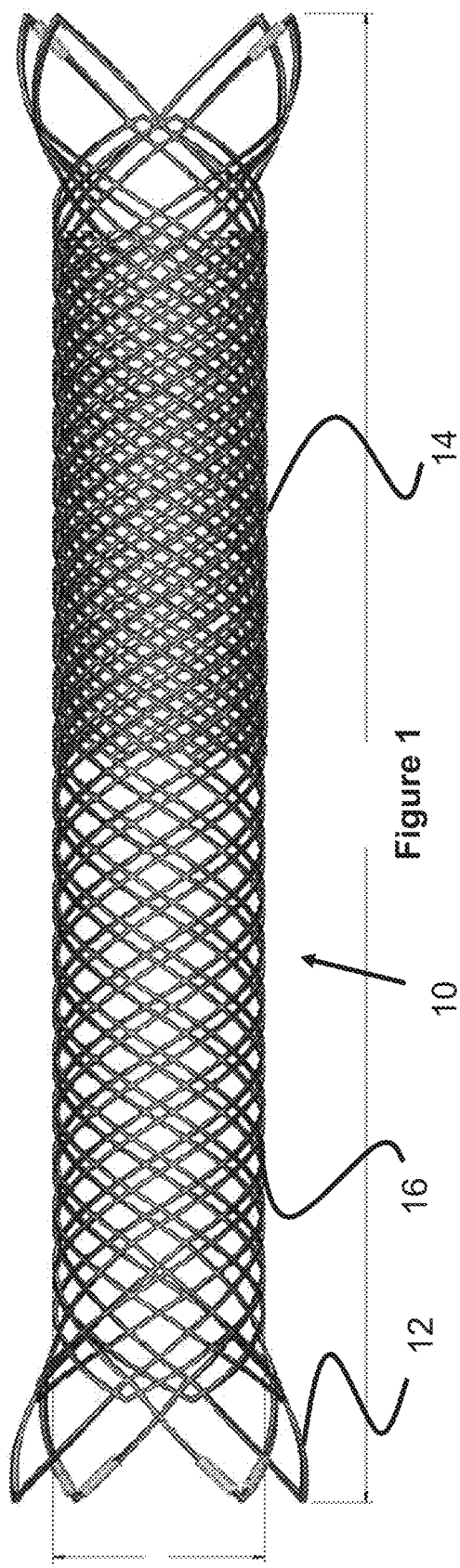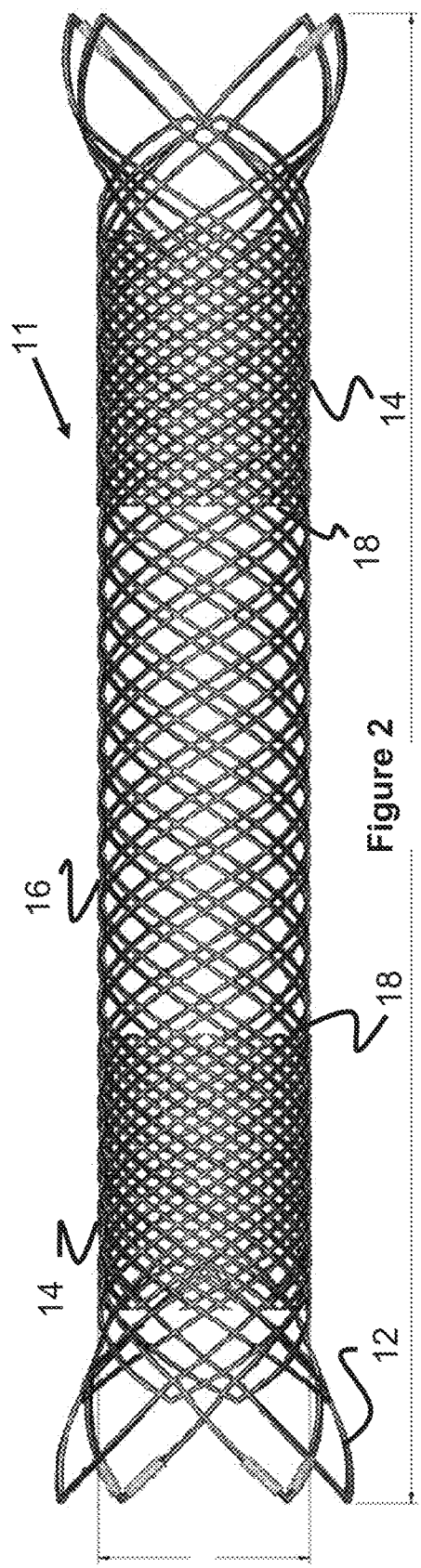

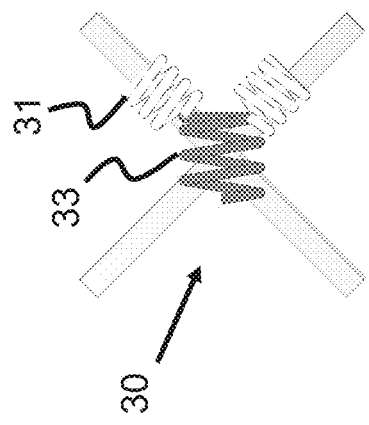
Figure 6A
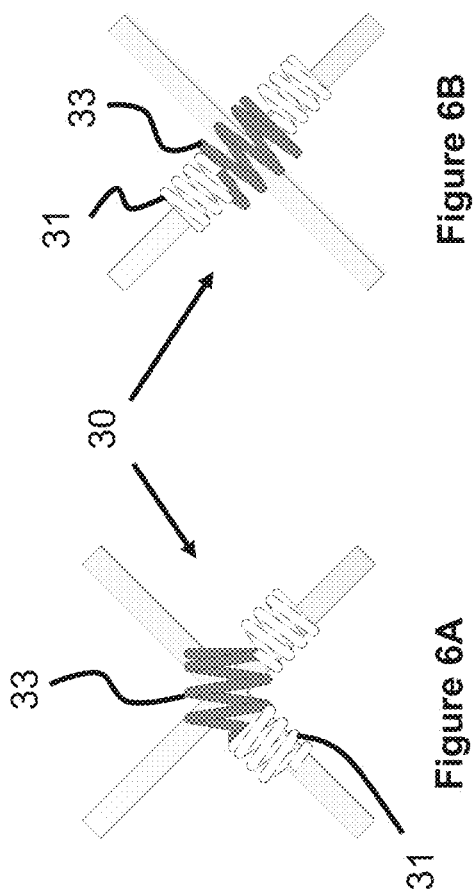
Figure 6B
Figure 6C
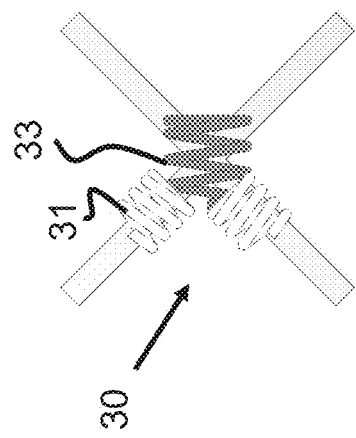
Figure 6D
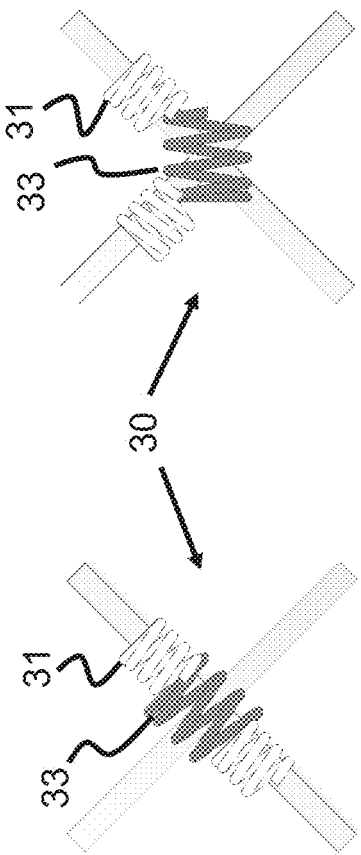
Figure 6E
Figure 6F

STENT

RELATED APPLICATIONS

This application is a continuation of and claims priority to U.S. patent application Ser. No. 14/994,024 filed Jan. 12, 2016 entitled Stent, which claims benefit of U.S. Provisional Application Ser. No. 62/102,483 filed Jan. 12, 2015 entitled Stent Designs, and U.S. Provisional Application Ser. No. 62/108,699 filed Jan. 28, 2015 entitled Stent Insert, all of which are hereby incorporated herein by reference in their entireties.

BACKGROUND OF THE INVENTION

Stents are used for various reasons within the vasculature, such as flow diversion or restoring blood flow where there is stenosis. The following specification relates to stent designs that could be used for a variety of situations including treating bifurcation aneurysms at a branch vessel, stent designs to augment the radial strength of braided stents, stents with regions of differing porosity, and methods of attaching stents together.

All of the following applications are hereby incorporated by reference in their entireties: U.S. Provisional Patent Application Ser. No. 61/422,604 filed Dec. 13, 2010 entitled Stent; U.S. Provisional Patent Application Ser. No. 61/425,175 filed Dec. 20, 2010 entitled Polymer Stent And Method Of Manufacture; International Patent Application No. PCT/US2010/061627, International Filing Date 21 Dec. 2010, entitled Stent; U.S. Provisional Patent Application Ser. No. 61/427,773 filed Dec. 28, 2010 entitled Polymer Stent And Method Of Manufacture 2; and U.S. Nonprovisional patent application Ser. No. 13/003,277 filed Jan. 7, 2011 entitled Stent.

The present invention relates to devices for the treatment of body cavities, such as the embolization of vascular aneurysms and the like, and methods for making and using such devices.

The occlusion of body cavities, blood vessels, and other lumina by embolization is desired in a number of clinical situations. For example, the occlusion of fallopian tubes for the purposes of sterilization, and the occlusive repair of cardiac defects, such as a patent foramen ovale, patent ductus arteriosis, and left atrial appendage, and atrial septal defects. The function of an occlusion device in such situations is to substantially block or inhibit the flow of bodily fluids into or through the cavity, lumen, vessel, space, or defect for the therapeutic benefit of the patient.

The embolization of blood vessels is also desired to repair a number of vascular abnormalities. For example, vascular embolization has been used to control vascular bleeding, to occlude the blood supply to tumors, and to occlude vascular aneurysms, particularly intracranial aneurysms.

In recent years, vascular embolization for the treatment of aneurysms has received much attention. Several different treatment modalities have been shown in the prior art. One approach that has shown promise is the use of thrombogenic microcoils. These microcoils may be made of biocompatible metal alloy(s) (typically a radio-opaque material such as platinum or tungsten) or a suitable polymer. Examples of microcoils are disclosed in the following patents: U.S. Pat. No. 4,994,069—Ritchart et al.; U.S. Pat. No. 5,133,731—Butler et al.; U.S. Pat. No. 5,226,911—Chee et al.; U.S. Pat. No. 5,312,415—Palermo; U.S. Pat. No. 5,382,259—Phelps et al.; U.S. Pat. No. 5,382,260—Dormandy, Jr. et al.; U.S. Pat. No. 5,476,472—Dormandy, Jr. et al.; U.S. Pat. No. 5,578,074—Mirigian; U.S. Pat. No. 5,582,619—Ken; U.S. Pat. No. 5,624,461—Mariant; U.S. Pat. No. 5,645,558—Horton; U.S. Pat. No. 5,658,308—Snyder; and U.S. Pat. No. 5,718,711—Berenstein et al.; all of which are hereby incorporated by reference.

Stents have also been recently used to treat aneurysms. For example, as seen in U.S. Pat. No. 5,951,599—McCrory and U.S. Pub. No. 2002/0169473—Sepetka et al., the contents of which are incorporated by reference, a stent can be used to reinforce the vessel wall around the aneurysm while microcoils or other embolic material are advanced into the aneurysm. In another example seen in U.S. Pub. No. 2006/0206201—Garcia et al. and also incorporated by reference, a densely woven stent is placed over the mouth of the aneurysm which reduces blood flow through the aneurysm's interior and ultimately results in thrombosis.

In addition to flow diversion and occlusion, the present invention can also be used in applications where high coverage or low porosity is desirable. For example, when treating carotid artery stenosis with a stent, emboli or particulates may be dislodged during stent deployment or post-deployment dilatation. Since these emboli can become lodged in the brain and cause a stroke, it is desirable to provide a stent with low porosity to entrap the particulates. Another application of a high coverage stent is in areas of the body prone to thrombus formation such as in coronary bypass grafts (also called saphenous vein grafts or SVG) and arteries and veins in the lower extremities. Since the thrombus can dislodge and occlude downstream tissues, it is desirable to deploy a high coverage device of the instant invention to cover and/or entrap the thrombus to prevent it from migrating.

SUMMARY OF THE INVENTION

In one embodiment a stent with at least one lower porosity and at least one higher porosity region is described.

In another embodiment a stent with at least one lower porosity and at least one higher porosity region is comprised of multiple stents of differing porosity being adjoined together.

In another embodiment a stent with at least one lower porosity region and at least one higher porosity region is used to treat a bifurcation aneurysm.

In another embodiment a stent with at least one high porosity region is used to introduce another stent through said high porosity region in order to treat a bifurcation aneurysm.

In another embodiment a braided stent utilizes selectively thickened regions to increase stent strength.

In another embodiment multiple stents may be attached together to create one stent.

In another embodiment stents of differing porosities may be attached together to create one stent with regions of differing porosity.

In another embodiment, wire ends of a braided stent are welded together.

In another embodiment a braided stent has a wire wound helically through the stent to aid in visualization.

In one embodiment an insert that can be used with a stent is described.

In another embodiment a single layer stent utilizing an insert is described.

In another embodiment a dual layer stent utilizing an insert is described.

In another embodiment a multiple layer stent utilizing an insert is described.

In another embodiment a drug-eluting insert, which can be used with a stent, is described.

In another embodiment a single layer stent utilizing a drug-eluting insert is described.

In another embodiment a dual layer stent utilizing a drug-eluting insert is described In another embodiment a multiple layer stent utilizing a drug-eluting insert is described.

Another embodiment is directed to a tubular shape formed from at least one woven wire; the tubular shape having a first region that is woven to have a first porosity and a second region that is woven to have a second porosity that is higher than the first porosity.

Another embodiment is directed to the previously described stent in which the first region is woven with a first braid pattern and the second region is woven with a second braid pattern.

Another embodiment is directed to the previously described stent in which the first region is woven with a higher pick per inch than the second region.

Another embodiment is directed to the previously described stent in which the at least one woven wire has a larger diameter within the first region than in the second region.

Another embodiment is directed to the previously described stent in which the first region and the second region are formed by simultaneously weaving the at least one woven wire on a single stent mandrel.

Another embodiment is directed to the previously described stent in which the first region and the second region are separately woven and then longitudinally attached together to form the tubular shape.

Another embodiment is directed to the previously described stent in which the first region and the second region are welded together.

Another embodiment is directed to the previously described stent in which the first region and the second region are attached via a plurality of mechanical ties.

Another embodiment is directed to the previously described stent in which the first region further comprises a plurality of mechanical ties, each of which connect a first stent wire and a second stent wire overlapping the first stent wire.

Another embodiment is directed to the previously described stent in which each of the plurality of mechanical ties further comprises a first coil having a first inner diameter and that is disposed around only the first stent wire.

Another embodiment is directed to the previously described stent in which each of the plurality of mechanical ties further comprises a second coil having a second inner diameter that is larger than the first inner diameter; the second coil being connected to the first coil.

Another embodiment is directed to the previously described stent in which the second coil is disposed around the first stent wire and the second stent wire.

Another embodiment is directed to the previously described stent in which the second coil is disposed around only the first stent wire.

Another embodiment is directed to the previously described stent in which each of the plurality of mechanical ties further comprise a third coil having a third inner diameter equal to the first inner diameter; the third coil being disposed around only the first stent wire.

Another embodiment is directed to the previously described stent in which each of the plurality of mechanical ties further comprise a third coil having a third inner diameter equal to the first inner diameter; the third coil being disposed around only the second stent wire.

Another embodiment is directed to the previously described stent in which the first region and the second region are separately woven and then longitudinally attached together to form the tubular shape; wherein stent wire of the first region is connected to stent wire of the second region via a coil.

Another embodiment is directed to the previously described stent in which free ends of the stent wire of the first region and the second region terminate with an enlarged portion and wherein the enlarged portion is larger in diameter than the coil.

Another embodiment is directed to the previously described stent in which the at least one woven wire comprises a plurality of wires, and wherein the wires each terminate with an eyelet connected to an eyelet of an adjacent wire.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIGS. 1-2 show a stent with regions of different porosities.

FIGS. 6A-6F show ties used to bind one or more wires of a braided stent.

DESCRIPTION OF EMBODIMENTS

Figure 3:
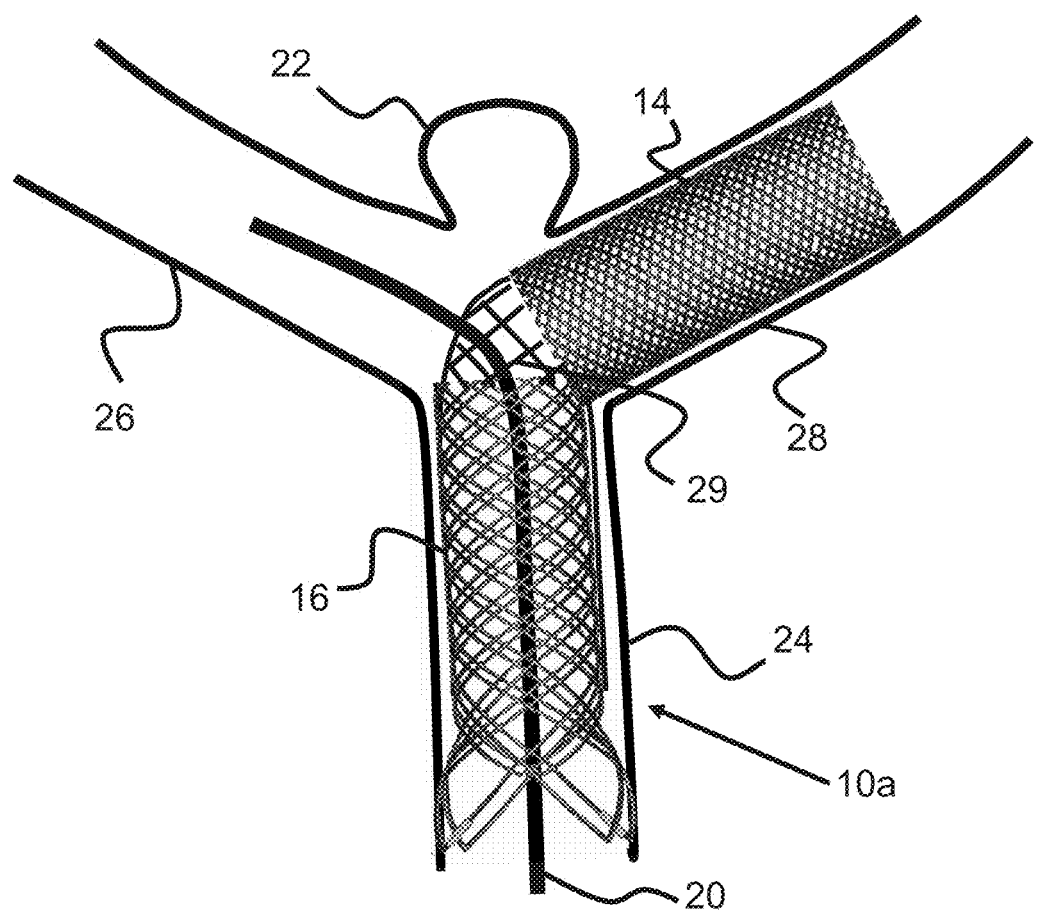
FIGS. 3-4 show the stent of FIG. 1 used to treat a vessel bifurcation aneurysm.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The embodiments and methods of the present invention can be used in connection with those disclosed in U.S. Pub. No. 2012/0259404 and U.S. Pub. No. 2013/0245745, which are hereby incorporated by reference in their entirety.

In one aspect of the present invention, a woven or braided single-layer stent includes different regions woven to have either a relatively high porosity or a relatively low porosity. For example, FIG. 1 illustrates a woven stent 10, optionally having distal end loops 12, that includes one high porosity region 16 and one low porosity region 14.

Preferably, the porosity difference can be controlled by the inclusion of additional layers. For example, the high porosity region 16 of FIG. 1 could solely comprise a highly porous outer layer while region 14 comprises a low porosity inner layer along with a high porosity outer layer. Thus the high porosity outer layer spans the length of the stent while the low porosity inner layer solely spans the low porosity portion of the stent. Such a stent may be manufactured by fixing or connecting the inner layer within a region of the outer layer. Alternate embodiments could utilize a high porosity inner layer and a low porosity outer layer. The high porosity portion (e.g., the outer stent layer) can have a pore size in the range of 0.016 inches-0.5 inches, and preferably 0.04 inches-0.2 inches. The low porosity portion (e.g., the inner stent layer) can have a porosity of about 0.004 inches-0.012 inches. Note that porosity is described in more detail with regard to FIG. 7 below.

Alternately, the porosity of the different regions of the stent are determined by the number and size of the wires comprising the braid, as well as the pattern of the braid (e.g., a first braid pattern and a second braid pattern). Generally, a stent with a high number of wires (e.g., high picks per inch) and/or a stent with a relatively small diameter wire will be less porous than a stent comprised of a smaller number of wires and/or small diameter wires (if all other variables are generally equal). In the context of this application, porosity refers to the open space through the wall of the stent. In the present embodiments, the porosity is created with the open gaps between wire crossings of the braid pattern. A highly porous segment will typically have large open gaps for blood to flow through, while a low porosity segment will have smaller open gaps for blood to flow through. In FIG. 1, this porosity difference can be created by using less wires in the high porosity region 16 than the low porosity region 14 of the stent 10. However, the porosity difference can be achieved by other factors, such as wire diameter or braid pattern.

The porous section 16 of the stent 10 in FIG. 1 may be located on either the proximal or distal end, depending on where the treatment area of the vessel is relative to the stent and deployment location. In one example, when the stent 10 is used to treat an aneurysm in a blood vessel positioned proximal to several feeder vessels, it would be desirable to have the more porous section of the stent located at a proximal end of the stent, so as to not block blood flow to the feeder vessel, while the less porous section is located at the distal end of the stent, so as to be positioned over the aneurysm opening to block blood flow into the aneurysm. In this respect, a stent configuration having a more porous proximal section and a less porous distal section is desirable.

In another example, if the stent is used to treat an aneurysm in a blood vessel and feeder vessels are located distal to the aneurysm, then it would be desirable to have a less porous proximal section of the stent to limit blood flow to the aneurysm and have a more porous distal section to allow blood flow to the feeder vessels. Such a stent would be particularly desirable where the aneurysm is located close to the feeder vessels, where it would be difficult to size a stent so that it is located contacts the aneurysm section but not the feeder vessel section of the vasculature.

In FIG. 2, stent 11 is shown with two low porosity regions 14 and one high porosity region 16 in between.

In one embodiment the stents 10, 11 are braided in such a manner as to incorporate these various regions of differing porosity, as discussed above (e.g., simultaneously woven as a whole, single stent on a single stent mandrel). In another embodiment, the stent 10, 11 are comprised of multiple stent segments that are separately braided and then attached together at attachment location 18. In one example the stent segments can be mechanically tied together (e.g., with tantalum wire ties). In another example, the stent segments can be welded together (e.g., laser welded). In yet another example, the stent segments can be bound together via adhesive. In another example, a combination of two or more of mechanical ties, welding, and/or adhesive bonding can be used to affix the stent segments longitudinally together into a single unitary stent.

Figure 4:
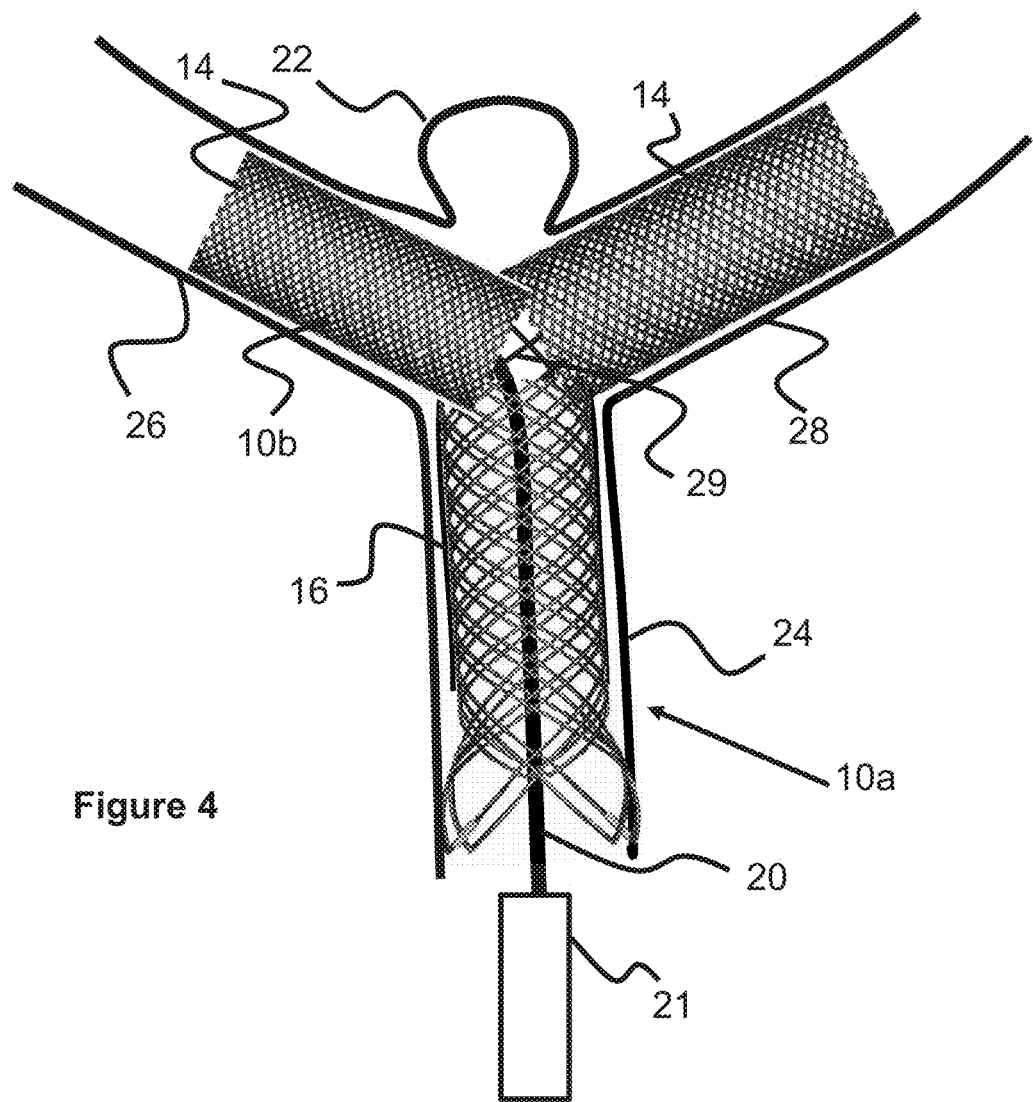

FIGS. 3-4 show a bifurcation aneurysm. The aneurysm 22 is located at a vessel junction in which there is a main vessel 24 that branches into vessels 26, 28. In this respect, the aneurysm 22 is located at the nexus of these vessels. Since it is desirable to divert blood flow to the aneurysm in order to minimize the risk of rupture y-stenting procedures are typically used. In such a procedure, multiple stents are placed within this y-portion of the vessels (area of vessels 26, 28, 24) in order to minimize blood flow to aneurysm 22.

In FIG. 3, a first stent 10a (similar to stent 10 described above) is deployed within one branch of the vessel. The low porosity region is located within a portion of vessel 28 and also overlies a region under aneurysm 22. Proximal to this low porosity region 14 is a high porosity region 16. Region 16 includes a number of large sized pores 29 which are formed between the intersection of the various constituent wires comprising the braid. Guidewire 20 may be deployed to this vessel location and the stent 10a is then tracked over the guidewire 20. Guidewire 20 is then manipulated or advanced through pore 29 and into the other vessel branch 26.

Next, a second stent 10b is tracked through the first stent 10a via the guidewire 20 and placed within vessel branch 26, as shown in FIG. 4. These stents 10a, 10b are positioned such that their low porosity regions 14 overlap each other, thus reducing blood flow into aneurysm 22. The high porosity portion 16 of the stent 10a is used as a conduit for introducing the second stent 10b. The stent 10b can include only a low porosity region 14, or may also include a high porosity region 16 that overlaps with the high porosity region 16 of stent 10a.

In an alternative method of deployment, guidewire 20 is first navigated to branch vessel 28. A microcatheter 21 is advanced over the guidewire 20 and stent 10a is first deployed at a vessel junction via the microcatheter 21. The guidewire 20 is then advanced to a position shown in FIGS. 3-4 through region 29 of stent 10a. The microcatheter 21 is then advanced over the guidewire within region 29 and stent 10b is then deployed via the microcatheter 21. Since the microcatheter 21 is located within region 29, there is minimum contact friction between stents 10a and 10b. The microcatheter 21 can be positioned such that the proximal deployed end of stent 10b is located just within stent 10a, minimize the contact surface and contact areas between stents 10a and 10b. Alternatively, the microcatheter 21 may be position just outside stent 10a, allowing stent 10b to be deployed such that stent 10b is not placed within stent 10a.

In FIG. 4, the second stent 10b placed within vessel 26 only has a low porosity region 14, however this stent 10b may alternately have the same configuration as the stent shown in FIG. 3, with its own low porosity and high porosity region. Hence, the high porosity region is located proximal of the low porosity region (i.e. the high porosity region would be disposed within region 16 of the first stent 10a). In one example, the later deployed stent 10b is undersized so as to sit within the first deployed stent even when fully opened. In another example, the later deployed stent 10b is the same size as the first deployed stent and is constrained from expanding fully by the restraining force provided by the first deployed stent 10a.

Figure 5A:
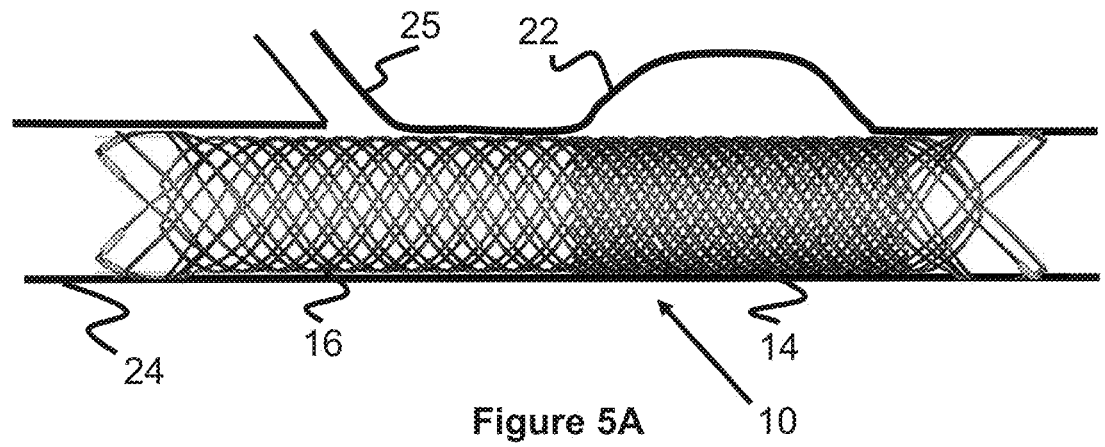
FIGS. 5A-5C show various conditions where a variable porosity stent would be useful.
Figure 5B:
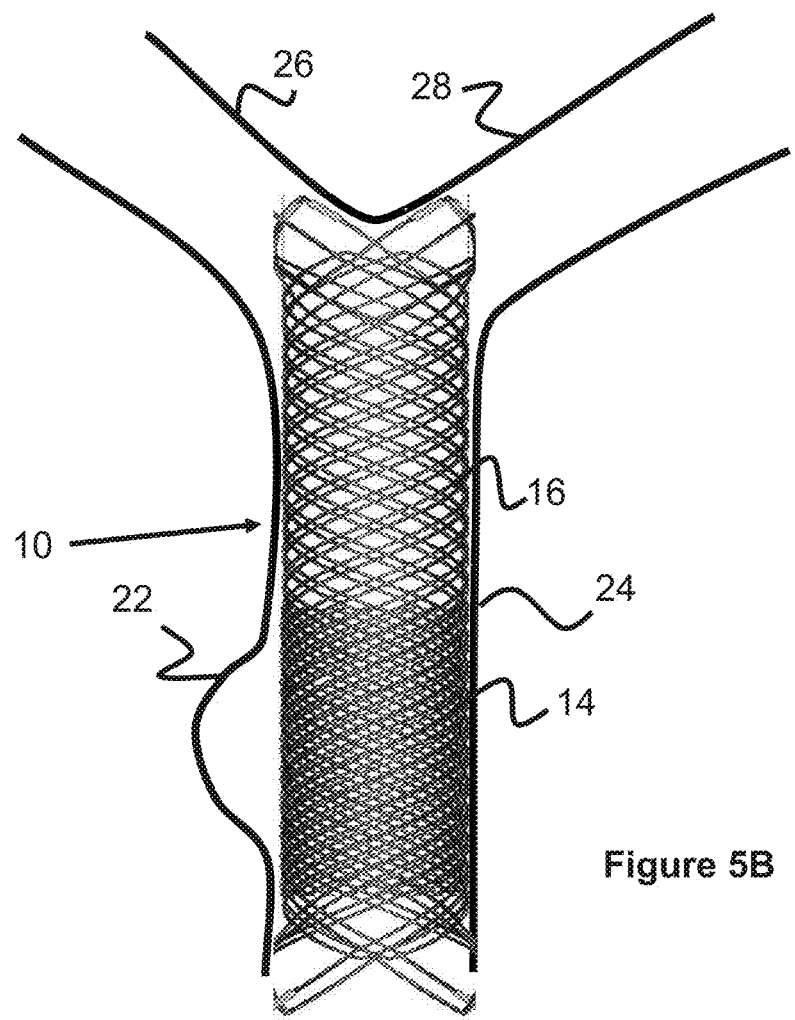
Figure 5C:
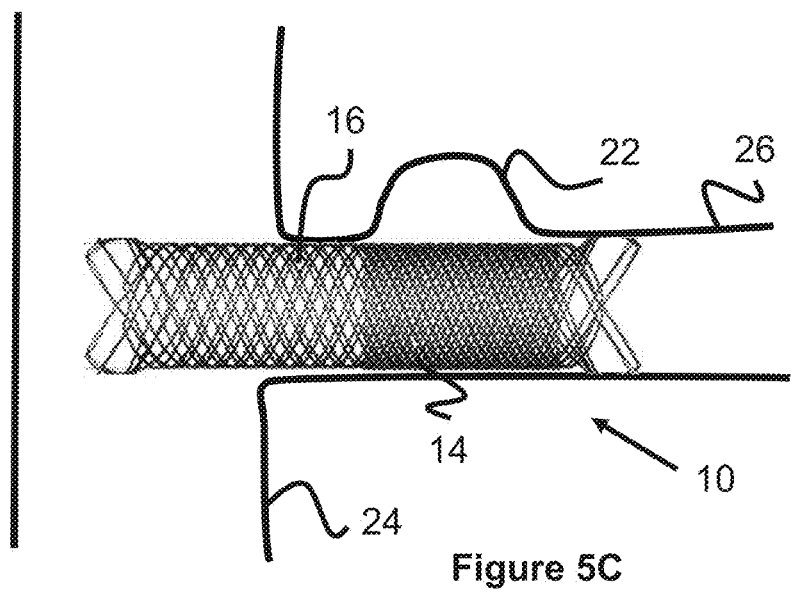

FIGS. 5A-5C show a variety of aneurysm locations where a stent 10 comprising a lower porosity section 14 and a higher porosity section 16 would be useful. In FIG. 5A, an aneurysm 22 bulges from a main blood vessel 24, adjacent to a small feeder vessel 25. The lower porosity portion 14 of the stent 10 covers and diverts flow to the aneurysm 22, while the higher porosity portion 16 of the stent 10 is disposed over the feeder vessel 25, allowing blood to flow through.

FIG. 5B illustrates an aneurysm 22 that bulges from a blood vessel 24 located near a bifurcation branch of vessels 26 and 28. The lower porosity portion 14 of the stent 10 covers and diverts blood flow into the aneurysm 22, while the higher porosity portion 16 is positioned towards and into the bifurcation to allow blood flow to pass into vessels 26 and 28.

FIG. 5C illustrates a main vessel 24 having a side branch vessel 26 with an aneurysm 22. Because the aneurysm 22 is located very close to the branch region, it may be difficult to place a stent that would not stick out from the branch region and into the main blood vessel 24. In this respect, the lower porosity region 14 can be positioned across the aneurysm, while the higher porosity region 16 can be positioned proximally so that, if the stent 10 is located outside the branch vessel 26 and fills the main vessel 24, the higher porosity region 16 would still allow blood flow within the vessel 26.

It should be noted that braided stents offer some advantages over laser-cut stents. For example, since braided stents are typically less thick then their laser-cut counterparts (the braided wires can be generally thinner than a laser-cut tube), they are typically more flexible. The strength and flexibility of braided stents can typically be customized by controlling various factors (i.e. wire diameter, pick count and density (typically measured as PPI, or pick per inch) within the braid, number of wires used, braid pattern, etc.). However, braided stents may lack the overall strength of laser-cut stents due to the generally thicker or more-dense profile of laser-cut stents.

Thickness or density of a braided stent can be increased (thereby increasing its strength) by including mechanical ties at intersection points along the braid, thus increasing strength at these junctions. While braided stents are comprised of one or more filaments braided or woven together to create a stent, laser cut stents are comprised of a solid material which is subsequently laser cut. Since the laser cut stents are comprised of a solid material, force is effectively transmitted through the stent, similar to force to a spring, thus these stents tend to act more spring-like than a braided stent and transmit force through the stent in a more effective manner. This quality is useful in stent deployment, where the push force is transmitted in an effective manner through the stent when it is pushed from the catheter. This quality is also useful to prevent stent migration since the stent, similar to a spring, will have its own internal force resisting displacement.

These ties also provide a spring-like effect where a coiled type tie is used, since a coiled tie will in effect act like a spring in these localized junctions where the ties are located. Thus, the stent will also adopt a springier material quality which would be useful for stent deployment as well as allowing the stent to resist migration. Alternately, a metallic or polymeric sleeve can be used instead of a mechanical tie to impart additional strength to the stent.

FIGS. 6A-6F show various configurations of a mechanical tie 30 used around intersection points of a braided stent. The mechanical tie 30 preferably includes two smaller coils 31 (e.g., have a relatively smaller inner diameter sized to fit around the stent wire) that are connected to a larger coil 33 (e.g., an inner diameter generally sized large enough to encompass two stent wires). The smaller coils 31 can be wrapped around either the same wire of the stent, on either side of a crossing wire (seen in FIGS. 6B and 6D), or can be located adjacent to each other on different stent wires that cross each other (seen in FIGS. 6A, 6C, 6E, and 6F). The larger coil 33 is preferably wound around two crossing stent wires and is further anchored in place via connection to the two smaller coils 31. Additionally, it should be noted that the two smaller coils 31 can either be connected to the free ends of the larger coil 33 (FIGS. 6A, 6B, 6D, and 6E) or they can be connected to one side of the larger coil 33 (FIGS. 6C and 6F). Alternately, the smaller coils 31 and the larger coil 33 can be fixed at or near crossing stent wires, but without connecting to each other. In addition to being wrapped around the stent wires, the ties 30 and/or their components can be fixed in place via adhesive, welding, or similar mechanisms.

The tie placement impacts the movement of the crossing stent wires relative to each other, thereby reducing flexibility between the wires due the restraining force provided by the ties. In this respect, the tie patterns shown in FIGS. 6A-6F all offer various advantages in terms of allowing some movement in the portion of the wires not enveloped by the ties while mitigating movement in another portion of the wires enveloped by the ties.

The ties 30 can be comprised of various materials such as tantalum, nitinol, stainless steel, cobalt-chromium, polymer, or combinations therein. One advantage of a radiopaque material, such as tantalum, used for the tie is augmented visibility of the stent in vivo. The material can also be selected to produce the desired stent characteristic. For example, if high strength is desired, a relatively stiff tie material can be used. If a more spring-like effect is desired, a more malleable material may be used.

Figure 7:
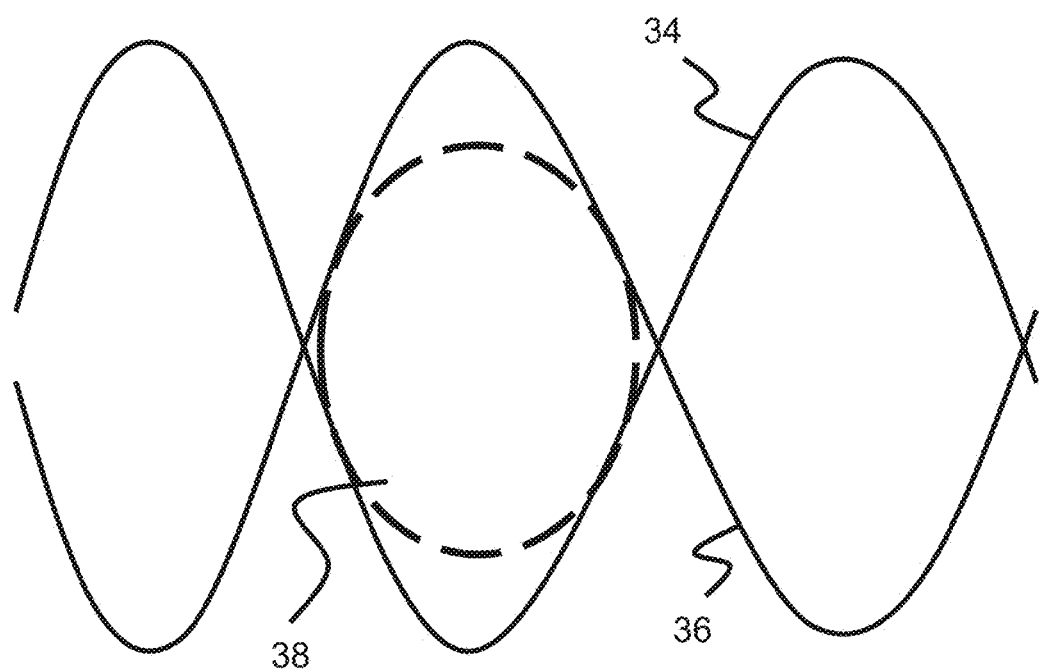
FIG. 7 shows a pore associated with a stent.

FIG. 7 illustrates a magnified view of several wires of the braided wire stent 10. The gap between wires 34 and 36 preferably forms a particular pore size, generally represented by circle 38. In one example the wires are braided to form a particular pore size, where the pore size is equal to or larger than the diameter of the microcatheter to allow the microcatheter to pass through the pore, as previously described with regard to FIG. 4. In one example, the pore size is about 0.01-0.03 inches. This pore size can either be relatively consistent throughout the stent, or can be localized to one region of the stent which is specifically meant to accommodate a microcatheter.

Figure 8:
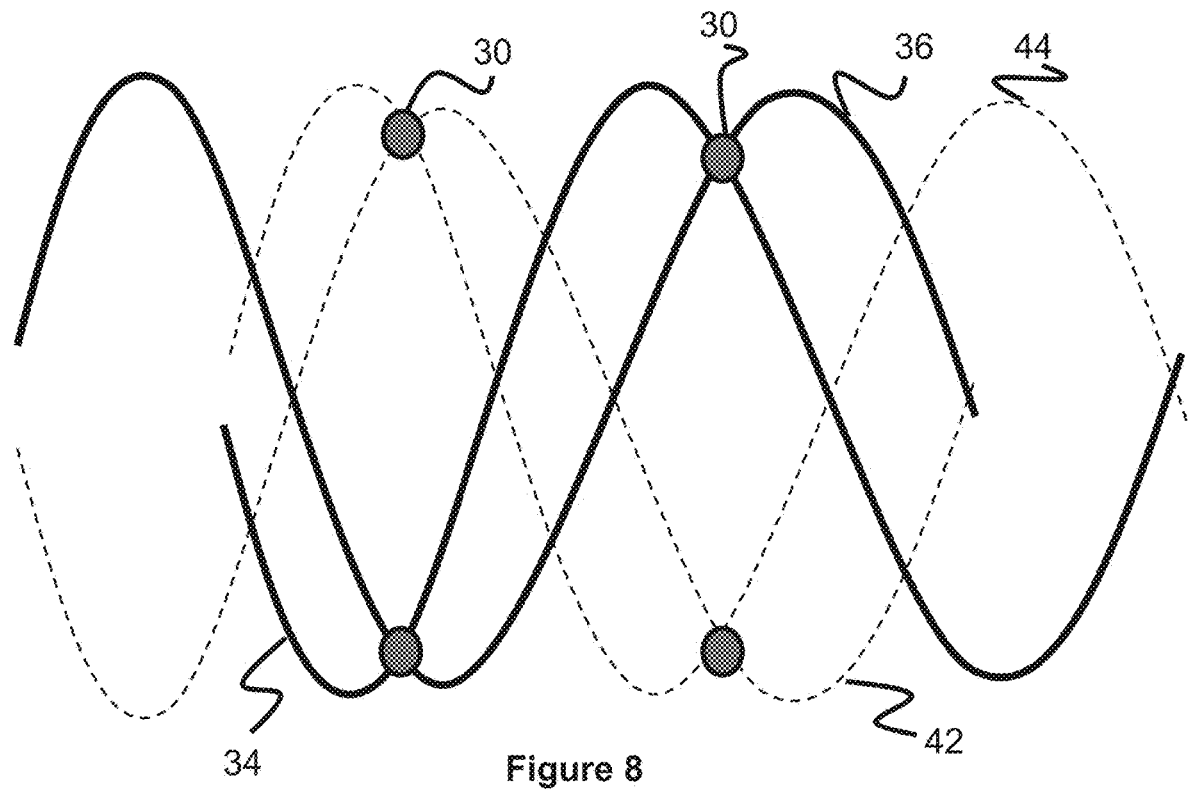
FIGS. 8-10 show a braided stent with ties.

FIG. 8 shows a magnified portion of a braided wire stent comprising two sets of braided wires—one pair 34, 36 and another pair 42, 44. The wires cross over or intersect, and are further connected with ties 30, as discussed earlier in this specification. Additional wires can also be used braided with these wires, such as 8-32 wires or 16 wires. The ties 30 may either be used at every intersection points or otherwise placed periodically throughout the stent in areas of the stent where increased strength is desirable. The wires are movable between the tied intersection points 40, but the ties act to anchor the wire crossing points thus preventing any slippage or movement of one wire with respect to the other at these intersection points. These tie points generally provide increased radial force due to the restraining force they provide and therefore create a localized spring effect similar to that seen with laser-cut stents.

Variations of the ties 30 are also contemplated. In one embodiment, one of the wires braided stent wires has a relatively rough surface (either the complete length of the wire, or at selected portions where the wires overlap). The rough portion increases the friction of the wire, thus limiting the movement of the other wire overlapping and contacting the rough area. In another embodiment the rough wire is adhesively bonded to the other smooth wire to provide a restraining force without a mechanical tie. In another embodiment both overlapping stent wires have overlapping rough portions and/or are bonded to each other.

Figure 9:
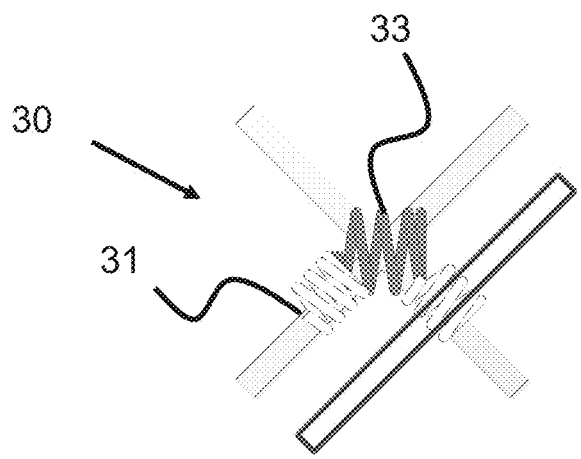
Figure 10:
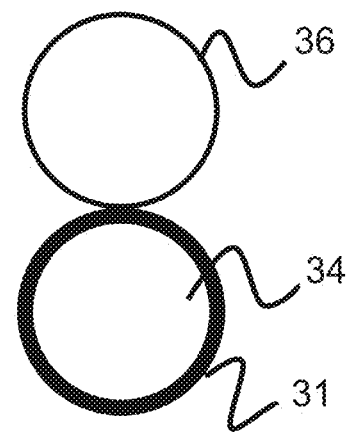

In another embodiment of the tie 30 illustrated in FIG. 9, the tie 30 connects to three or more stent wires, further augmenting the restraining force on the stent.

In another embodiment, the mechanical tie 30 is wound around one but not both overlapping stent wires 34, 36 at their intersection point. While this may provide less restraining force than if both wires 34, 36 were mechanically tied, it allows for greater flexibility while creating friction between the two wires 34, 36 (e.g., between the smaller coil portion 31 and the wire 36). In a further alternate embodiment, both wires 34, 36 include this tie 30 and an adhesive that bonds the ties together. Alternatively, the two wires are welded together or bonded together with adhesive at the junction where the wires meet.

FIGS. 1-4 and the associated specification discussed a stent with regions of different porosity comprised of stents of differing porosities which could be attached together. The following embodiments describe techniques of attaching multiple stents together to create a singular stent comprised of multiple sections.

Figure 11:
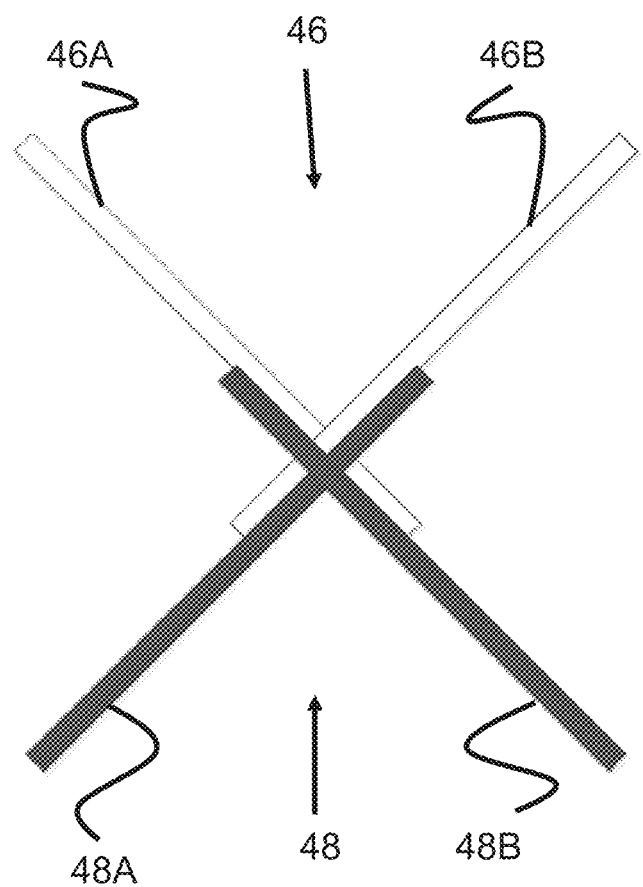
FIGS. 11-12 show a method of attaching two stents together.

Two stents or tubular, woven portions may be laser welded together in order to combine them and create a longer stent, as previously mentioned. FIG. 11 illustrates a magnified view of an example interface or connection point between two different woven portions of a stent. The wires of the stent portion 46, such as the two wires 46A and 46B, are welded to the wires of stent portion 48, such as wires 48A and 48B. Alternately, mechanical ties or adhesive bonding may be used in lieu of or in addition to welding. In one example, the attached stent portions have different porosities in order to create a stent with a longitudinally variable porosity profile (i.e. similar to the stents of FIGS. 1-2). In another example, the stent portions have a similar porosity and are attached together to create one longer stent with a similar porosity profile.

Figure 12:
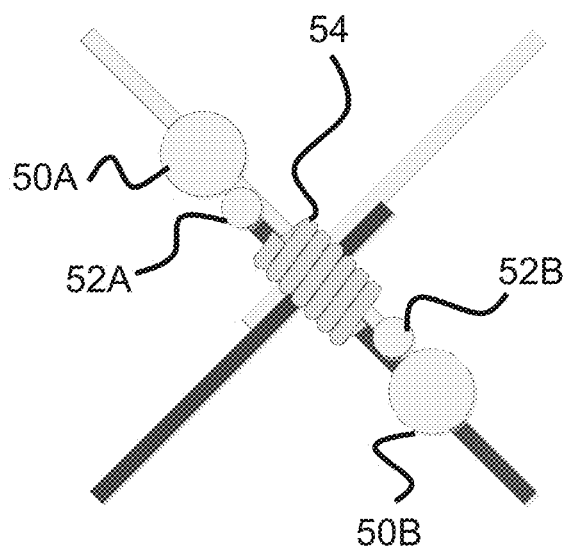

In lieu of laser welding, the wire ends may be bound together with a coil 54, as seen in FIG. 12. This connection technique imparts a small range of motion between the two wires, but still allows the wires to be attached. Each wire has an enlarged section 52A, 52B at the terminal end of the wire as well as a larger enlarged region 50A, 50B (e.g., a sphere, bulb, or similar shape) somewhere proximal of this terminal end. The coil 54 (or sleeve) is wrapped around the wires, between enlarged portions 52A and 52B such that these enlarged portions 52A, 52B are unable to be pulled through the coil 54. The larger, enlarged regions 50A and 50B create a stop or movement limiting feature that can contact the enlarged regions 52A and 52B, preventing wire movement beyond the regions 50A and 50B. In this respect, the wires may have a small degree of movement relative to each other (i.e., space between the coil 54 and the regions 50A and 50B.

It should be appreciated that the smaller enlarged region 50A, 50B proximal of the terminal end as well as the binding mechanism (e.g., coil or sleeve) are optional since the enlarged sections 50A-50B at the terminal end of each wire would provide a limit to how far one wire could slide relative to the other wire (e.g. the wires are freely slidable until one wire hits the enlarged section). However, the advantage of the binder (e.g., coil or sleeve) and the smaller enlarged regions 52A and 52B is that when the wires slide relative to each other up until they contact the enlarged sections 50A, 50B, the inclusion of the binder coil 54 around the wires ensures that the wires do not push radially outward in response to the contact force from the enlarged sections and thus disassociate relative to the enlarged sections, thereby restraining the radial movement of the wires. Smaller enlarged regions 52A and 52B limit the movement of binder 54 and thus prevent the binder from sliding off. Binder 54, in addition to a coil or sleeve, may be a coupling tube which is resistance welded.

Figure 13:
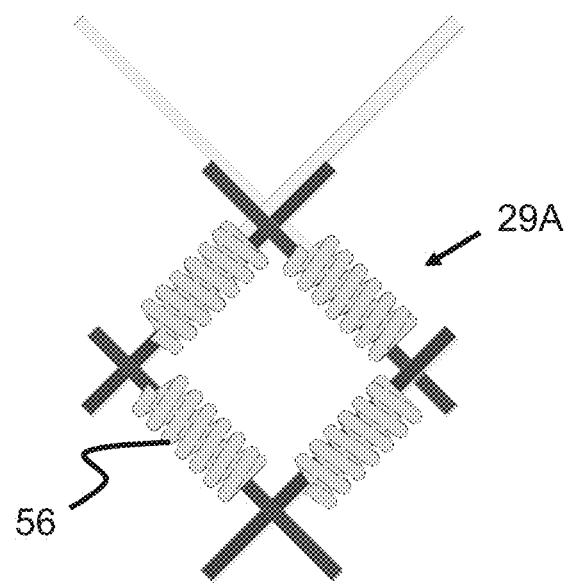
FIG. 13 shows a radiopaque section of a stent used to pass another stent through an opening within the section.

FIG. 13 illustrates another embodiment of a pore 29A through which a second stent can be delivered through (as previously discussed in this specification, such as FIGS. 3-4), which is formed by several radiopaque marker coils 56 that are placed over the wires surrounding region 29a, where the region 29a has a larger pore size region to accommodate the entry of another stent (i.e. for y-stenting purposes). Alternately, a marker band may be used. Region 29a may be located anywhere along the stent, and may comprise, for example, one cell of a stent or a portion of a stent where the portion comprises more than one cell. This concept can also be used for a low porosity stent where a portion of the stent has a pore size large enough to accommodate a microcatheter (i.e. for embolic delivery). The section of the stent with the larger pore size could be enveloped with radiopaque coil or marker bands so a user would know where to place the microcatheter through the stent. A radiopaque material, such as tantalum, can be used on the wires of the coils in the region around the pore 29 so that the user can visualize the region of the first stent which accommodates the second stent.

Though region 29a is described as having a larger pore size than the remaining pores of the stent in these examples, alternate embodiments are also possible. Region 29A may be loosely configured to allow the pore 29A to stretch to a larger size to accommodate the entry of another stent. Alternatively, the size of each of the pores throughout the stent can be large enough to accommodate the entry of another stent. That is, the stent has large pore sizes throughout the breadth of the stent sized to accommodate another stent's entry through the pores. Alternately, region 29A may have a larger pore size than the rest of the stent and may also be loosely configured to allow the pore size to stretch. This loose configuration can be made possible by not restricting the movement of the wires relative to each other in the region 29A, allowing the wires to move and accommodate the entry of another stent within the region. In one example, region 29a does not utilize adhesive, ties, or other binding mechanisms between the braid wires in the region in order to maximize free movement of the wires within region 29A.

Figure 14:
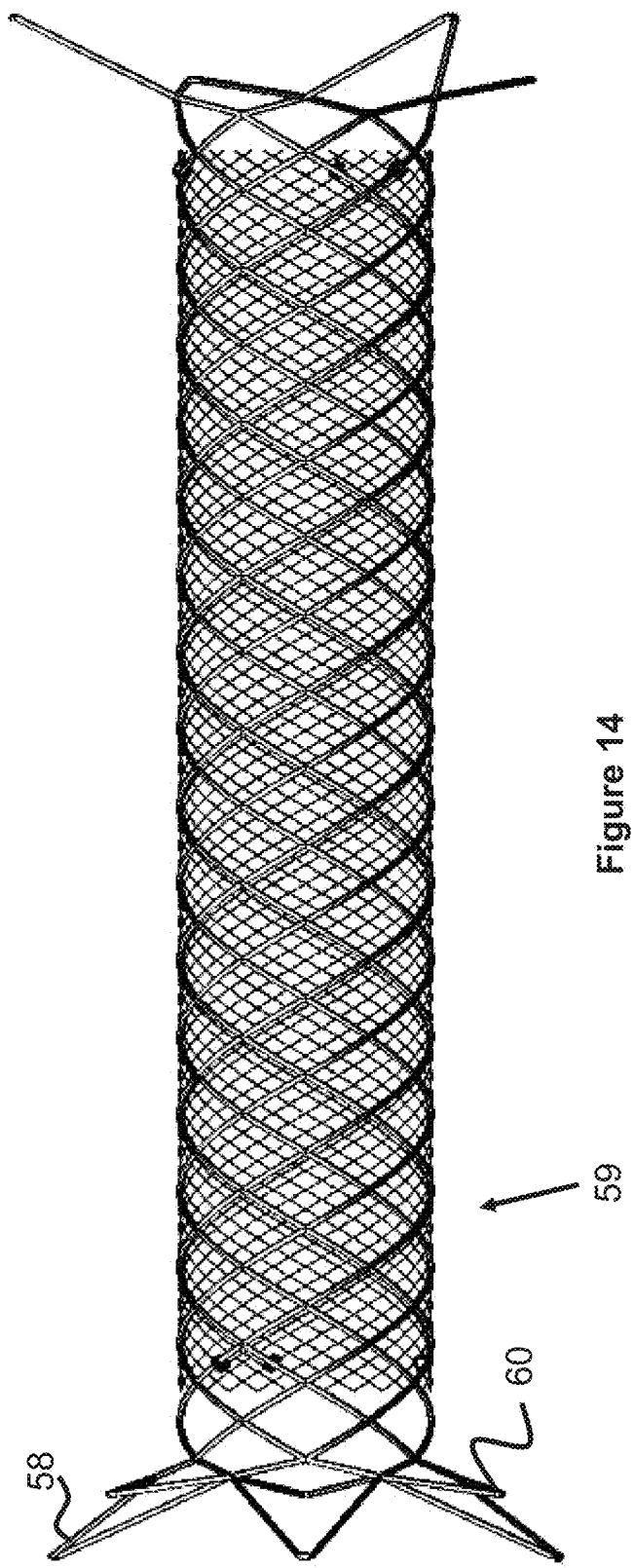
FIGS. 14-15 show a method of attaching two stents together where at least one of the stents has a portion with flared loops.

Some stents 59 utilize flared ends, as shown in FIG. 14. Some benefits of flared ends include increased retention or anchoring strength within the vessel. Attaching flared-end stents linearly together may due to the increased diameter and may provide further difficulties in maintaining a uniform diameter. Many options are available to attach these flared end stents 59 together. In one option, one end of the stent 59 is cut to eliminate the flare (e.g. keeping the flared loops on one end and cutting the stent at the other end to eliminate the loops) and then the next tent is attached at the cut point.

Figure 15:
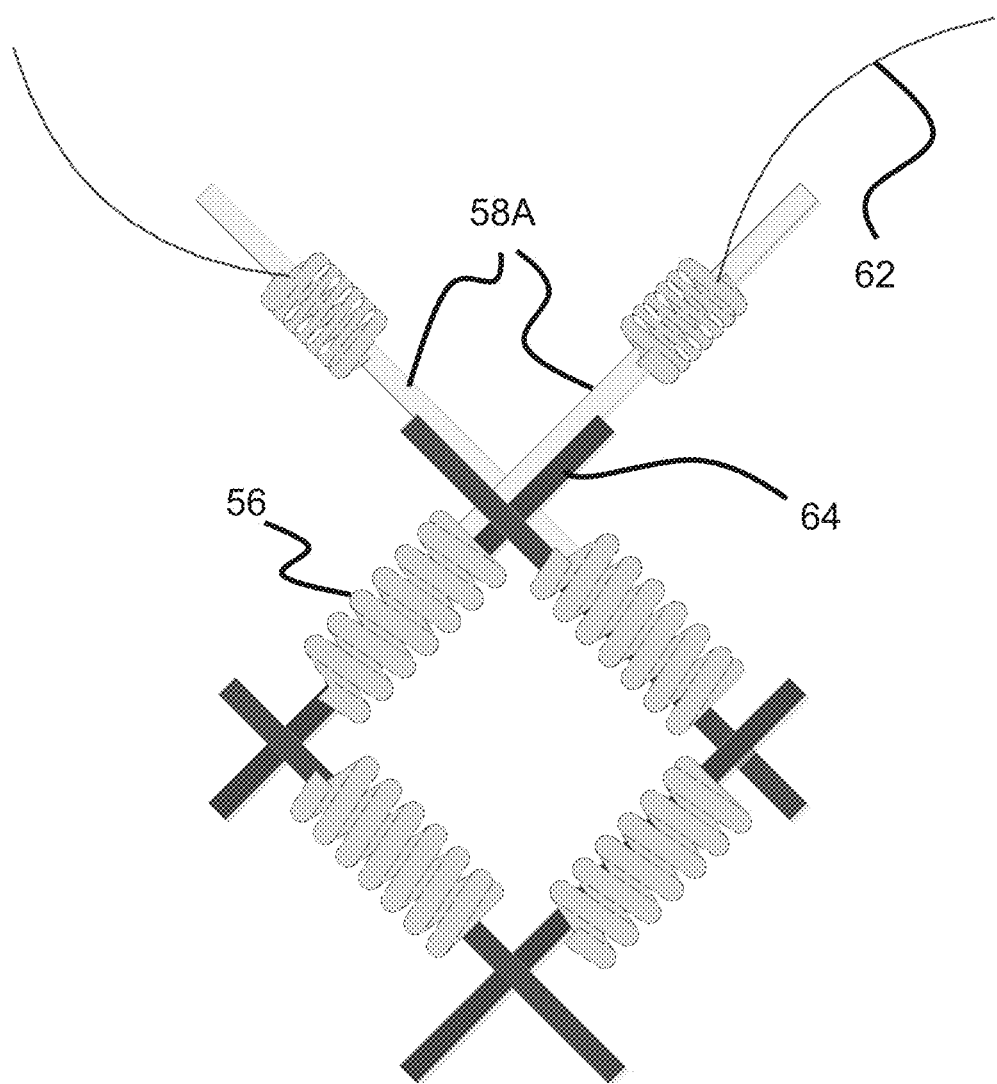
Figure 16A:
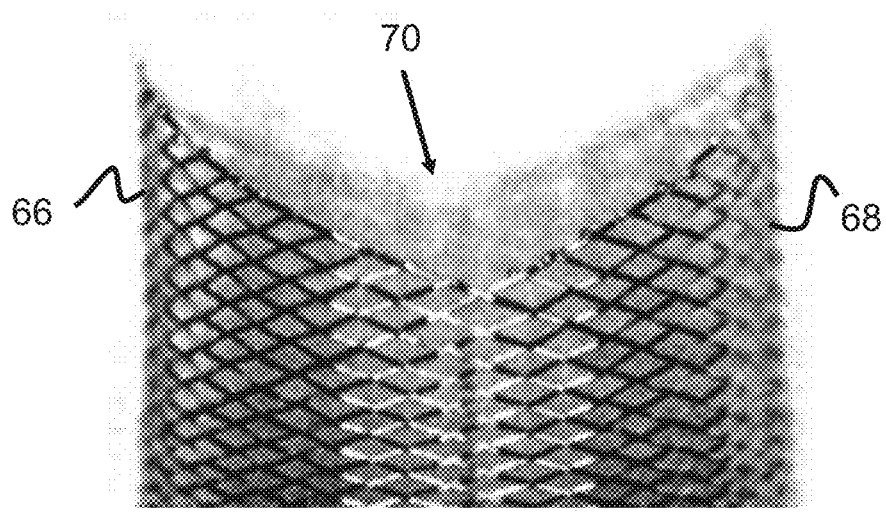
FIGS. 16A-16M show different patterns for welding together open wire ends of a stent.
Figure 16B:
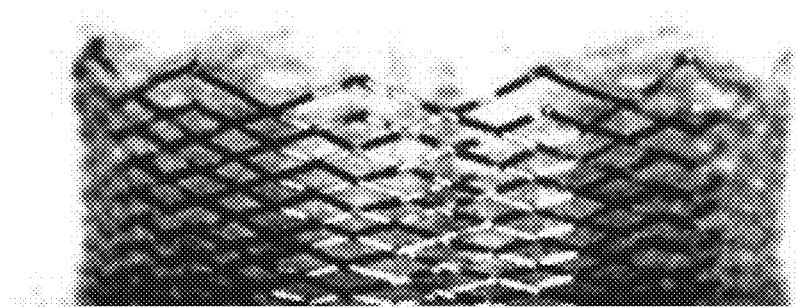
Figure 16C:
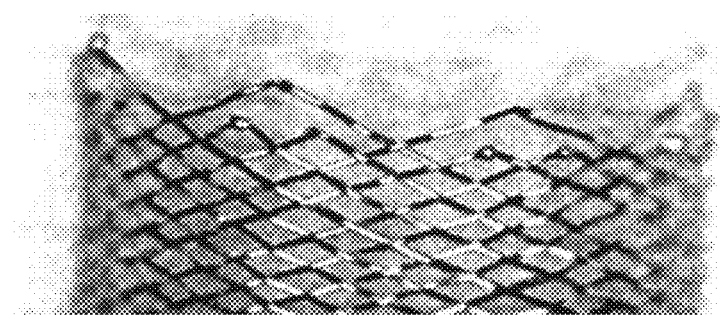
Figure 16D:
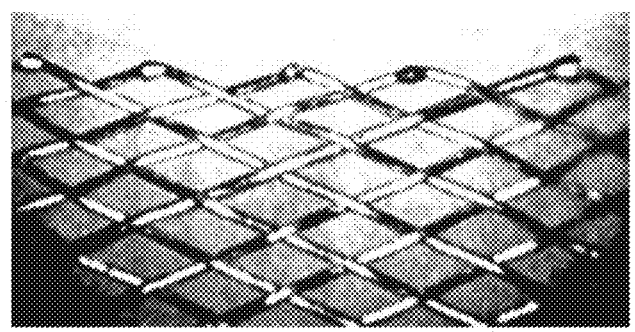
Figure 16E:
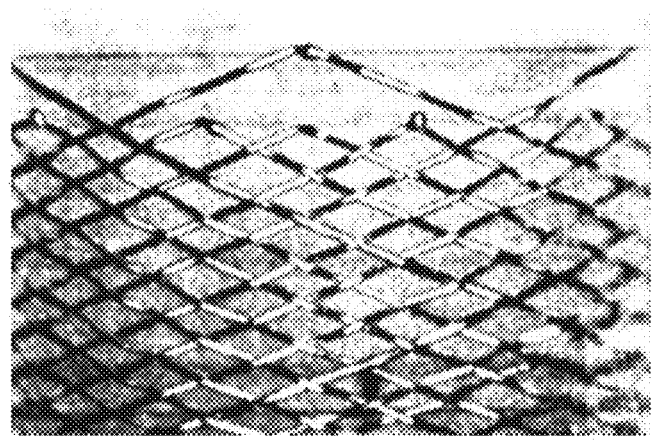
Figure 16F:
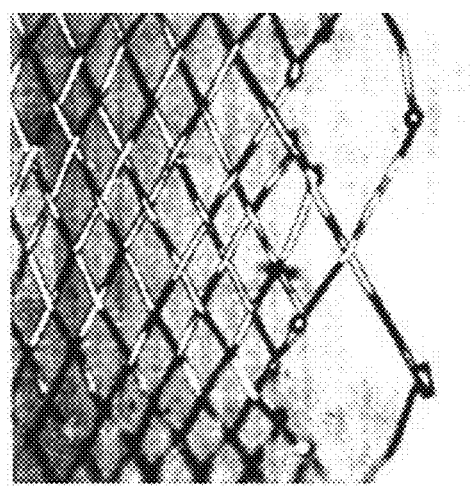
Figure 16G:
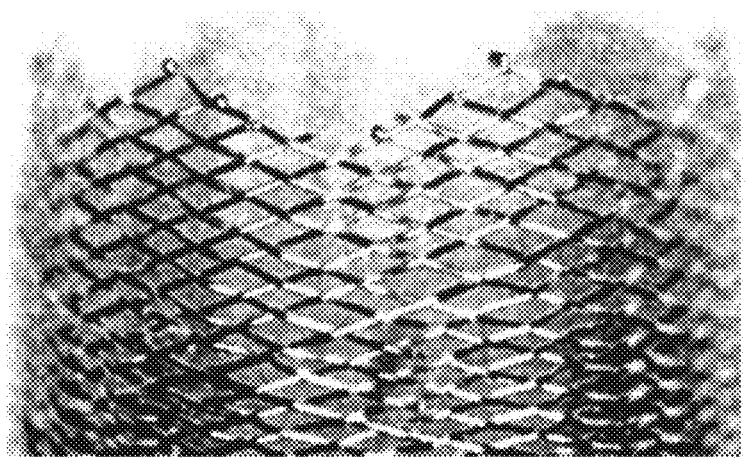
Figure 16H:
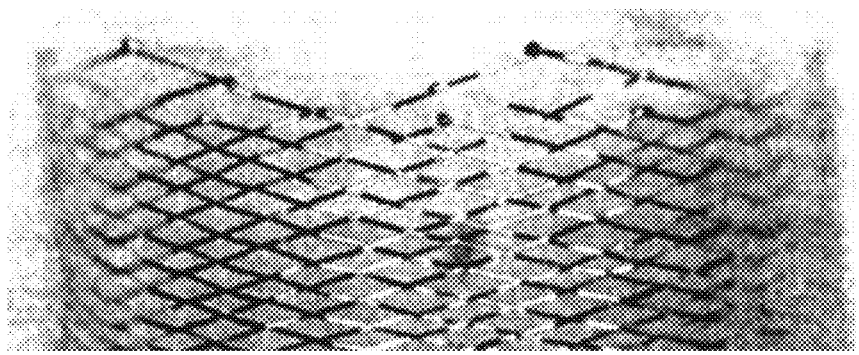
Figure 16I:
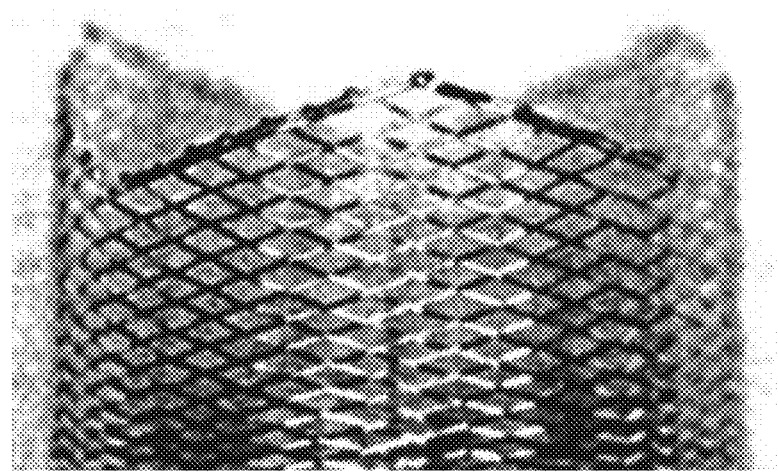
Figure 16J:
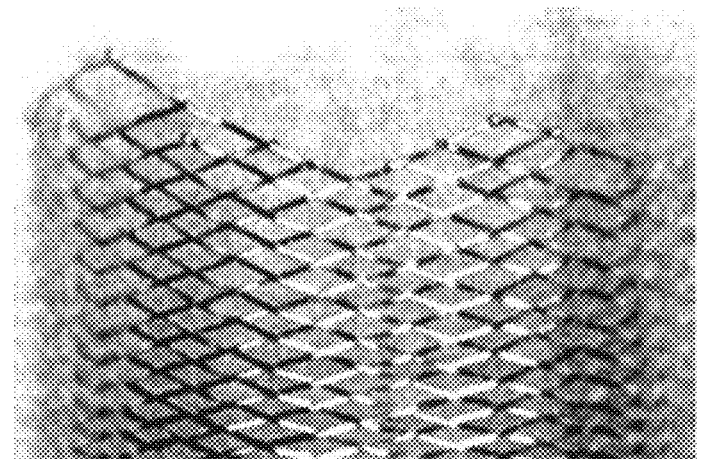
Figure 16K:
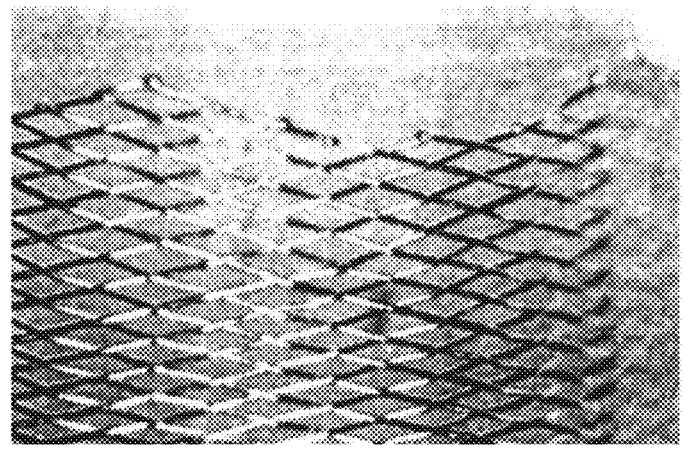
Figure 16L:
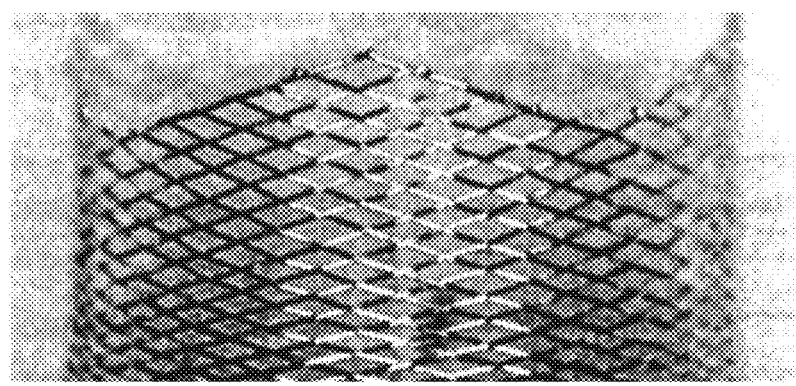
Figure 16M:
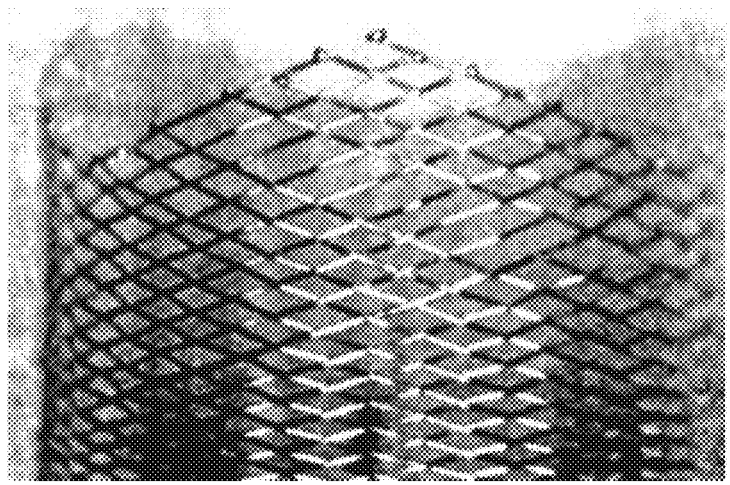

Another option to connect one or more flared ends of two stents together is shown in FIGS. 14-15. The stent has longer looped flares 58 (comprising three longer flares in the figure shown, though more or fewer flares are possible) and shorter flares 60 (comprising three shorter flares in the figure shown). In the figure shown the shorter flares and longer flares alternate, that is there is a longer flare next to a shorter flare next to a longer flare, etc. Wire 62 connects, at one end, to one short flare 60 and at the other end to one long flare 58. The wire can be welded, tied, or adhesively bonded to the flares. Alternatively, a system analogous to that described in FIG. 14 can be used to secure wire 62 to the wires of the flares. Since wire 62 is connected to both flares, a pulling action on the wire will cause both the short and long flare to collapse since the wire is connected to both flares.

In FIG. 15, element 58a identifies wire from one of the longer flares 58 of a first stent. The flare is preferably v-shaped and each of the two portions of the "v" has a wire 62 coiled onto or otherwise attached to it. For the example, in FIG. 14 in which three longer flares 58 and three shorter flares 60 are shown, only six wires 62 are used since each wire connects to one of the long flares and one of the short flares and two wires are used per flare. In other words, the number of wires 62 matches the total number of flares of the stent. Element 64 denotes wire from the second stent, and can be a flared element at one end of the stent or can be a non-flared section (i.e. the section where the flare is cut from the stent, as described earlier, or another stent which utilizes no flares). One advantage to using the large flare to connect the two stents as described is that the large flares, as can be appreciated from FIG. 15, has a relatively large pore opening. In this way, the large flare can be used similar to pore 29 in FIG. 3—that is, as a conduit through which another stent can be introduced for various purposes, such as y-stenting at a vessel bifurcation.

Note that two wire ends will meet at or near the terminal end of the flare. Thus a braid with 6 flares (i.e. 3 large flares, 3 small flares) will be comprised of a 12 wire braid. A braid with 8 flares (i.e. 4 large flares, 4 small flares) will be comprised of a 16-wire braid, and so on.

Although wire matching from one stent to another is not required when attaching two stents together, wire matching is generally desirable in order to ensure there are no loose, unattached wires which could protrude from the stent and cause vessel trauma (i.e. a 1:1 connection point between constituent wires in two different stents during attachment). For example, a wire braid comprising 12 wires would best be attached to another wire braid comprising 12 wires since each wire in one stent would attach to another wire in the other stent without any wires left over.

Where two stents with flares are joined together, the stents can be joined together at the flares. Where two stents with both large and short loop flares are joined together, the stents can be joined at the intersection where the large flares from one stent overlap with the large flares from the other stent. This is possible since the large flared section will tend to protrude outward more from the stent than, say, the short flare section. Alternately, the loop flares can be cut to expose the constituent wires comprising the loops and the wires can then be directly attached to each other in a 1:1 arrangement as described directly above.

The above description refers to the method of attaching two stents together where at least one stent may be cut. Stents may also be cut for several reasons. In one example a stent can be woven continuously over a mandrel and then cut in select sections to create multiple stents. However, where the stent is comprised of one or more wires, or a braid of wires, cutting the stent will cause open wire ends which may be traumatic within the blood vessel. Cutting the stent may also cause the wires to fray which may also be traumatic within the vasculature. The cut sections of the wires may be welded together to create a closed end configuration and minimize the trauma within the vasculature. The cut and weld pattern can take on a number of shapes, as shown in FIGS. 16a-16m. The closed end design also enhances retrievability of the stent after/during deployment by providing a closed region surface which a mechanical device could latch onto in order to retrieve the stent. In one embodiment, a dual layer stent comprising an inner and outer layer utilizes the closed end design on the inner layer of the stent. Mechanical ties (i.e. helical coil wraps, or other ties) could be used along the length of the stent to bind the inner and outer layer layers and ties could also be placed at/near the closed end regions to prevent one layer from shifting relative to another layer.

Figure 18:
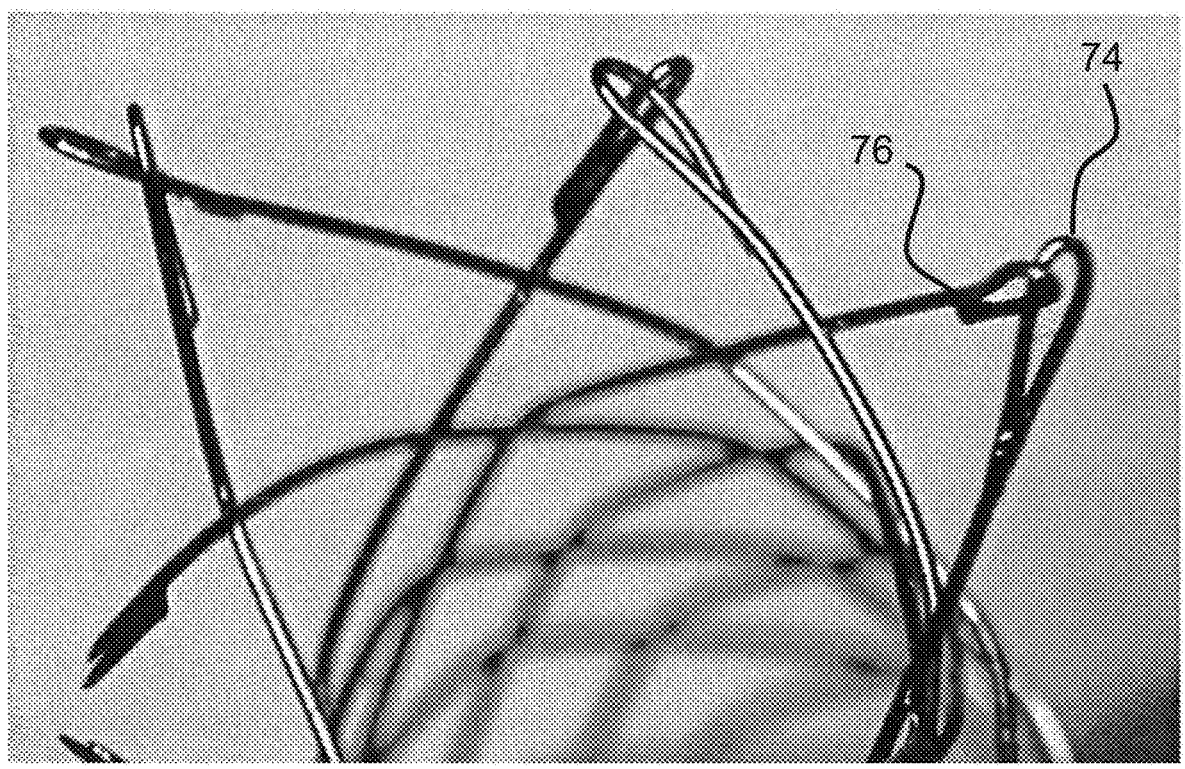
FIGS. 18-20 show alternate configurations to secure the ends of a stent/prosthesis together.
Figure 19:
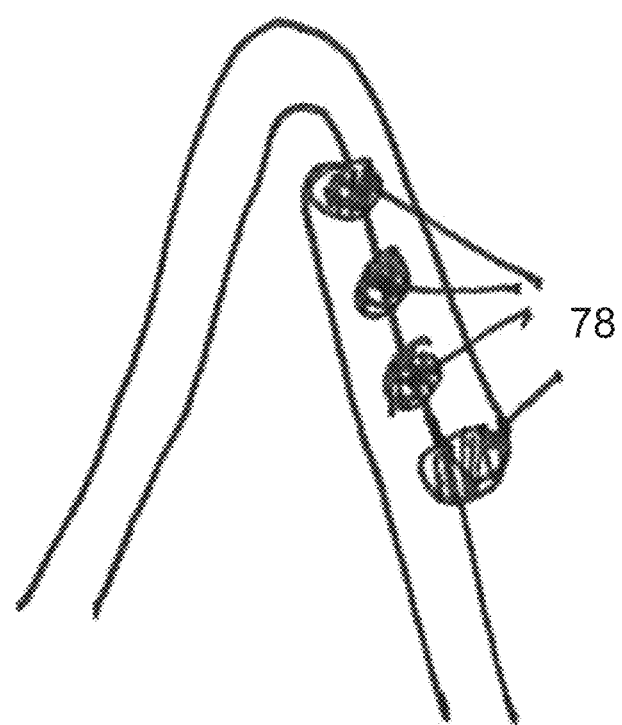
Figure 20:
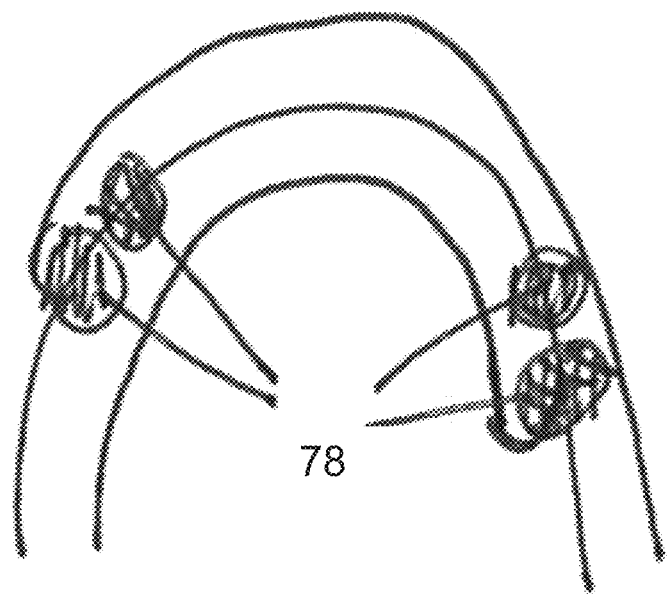

Alternate configurations to prevent frayed ends are shown in FIGS. 18-20. One embodiment shown in FIG. 18 involves the use of eyelets that connect to an adjacent eyelet. The wires comprising the outer layer of the stent/prosthesis are bent or shaped to form eyelets 74 by pulling the wire back onto itself and welding the wire at location 76. The eyelet of one wire end is first created and then the second wire is inserted into the eyelet of the first wire end, and finally the second wire is then welded at location 76 to create the second eyelet, thereby connecting the eyelets. The wires are also free to move a bit relative to each other, depending on the size of the eyelet region. Thus, this configuration offers some advantages in terms of flexibility of the stent/prosthesis.

Other variations involve pulling back one wire with respect to the other and welding the wires together. This arrangement is shown in FIG. 19, where the wires are welded together at one or more locations 78. Alternate configurations involve pulling back both ends of the stent and welding both stent ends to the other wire at a more proximal location, as shown in FIG. 20.

In a multiple layer braided stent (i.e. a dual layer stent with an inner and outer braid layer), either or both of the layers may utilize the weld configurations to reduce the trauma due to the open wire ends. In one example, an inner layer of the stent (see the dual layer stent of FIG. 16) is comprised of a braid which is cut at one or both ends, and the outer layer of the stent is comprised of a separate braid with flared loops at each end, where the outer layer is not cut at either end. The inner layer of the stent may utilize the welded ends in order to minimize vessel trauma. In one example, spot welding or any heat treatment which can introduce a rounded shape at the junction of the two combined wire ends is used in order to create a smooth profile at the wire ends to minimize potential vessel trauma. In another example, a stent is comprised of solely one layer of a braided material, the stent is cut at both ends, and the ends of the cut wires are welded together to prevent frayed or open ends in order to mitigate vessel trauma.

Figure 17A:
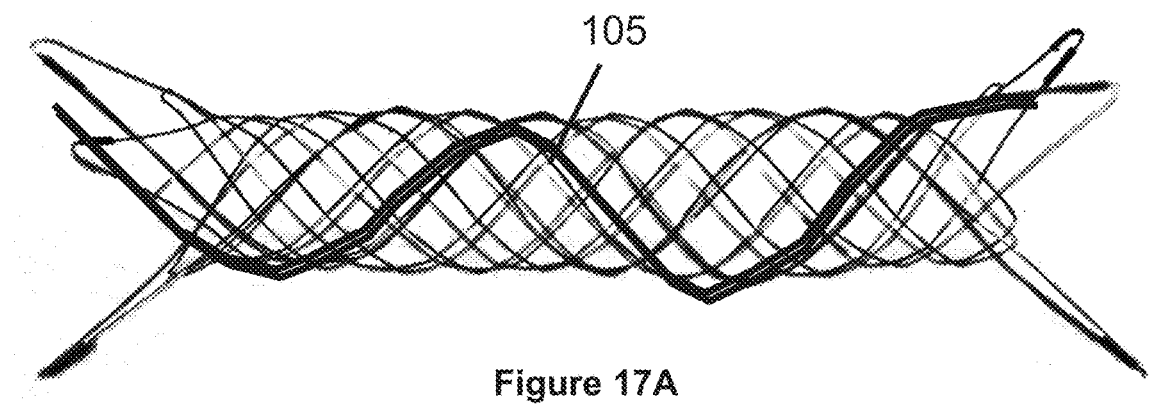
FIGS. 17A-17B show a wire wound through a stent.
Figure 17B:
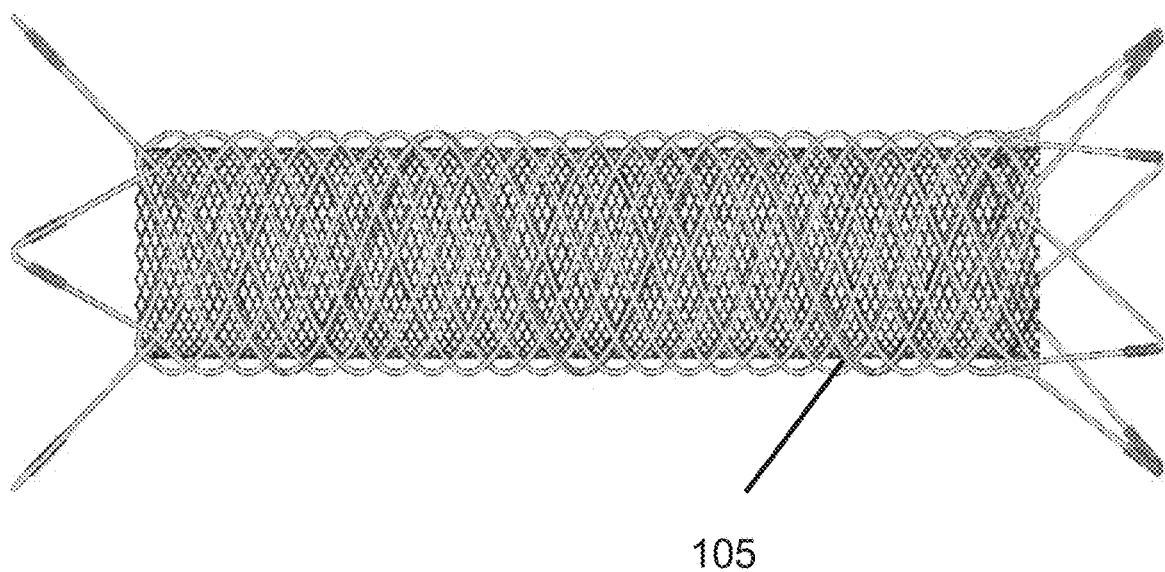

FIGS. 17A-17B illustrate a stent with a wire 105 wound helically through the stent. Preferably this wire is radiopaque (i.e. tantalum) in order to augment visualization of the stent in vivo. In FIG. 17A wire 105 is wound into a one layer stent, and in FIG. 17B wire 105 is wound through a two-layer stent comprising an inner layer braid and outer layer braid. Where wire 105 is wound through a two layer stent, the wire is wound through both layers in an over/under manner (i.e. over the outer layer, under the inner layer, etc.) thus binding both layers together.

Another wire may also be wound in an opposing manner, the wire can be comprised of nitinol or can be radiopaque (i.e. made of tantalum). The use of a second wire wound in an opposing manner is important when considering a welded stent end configuration such as that shown in FIG. 16A where the stent contains two protruding sections 66, 68 surrounding a cut-away section 70. Where wire 105 is wound within this stent in only one direction, either section 66 or 68 will not have wire 105 wound within the section due to the presence of cut-away section 70 reducing the external surface area through which the wire may be wound through the stent. In order to allow either section 66 or 68 to gain the benefits of radiopaque wire 105 (i.e. increased radiopacity), a separate radiopaque wire may be used within this section. Alternatively multiple wires may be used in this section (i.e. multiple radiopaque wires, or one radiopaque wire and one non-radiopaque wire). Alternatively, another wire can be wound in an opposing manner to wire 105. Since this second wire would be wound in an opposing manner, the wire would reach the section missing wire 105.

Flow diverting stents may effectively treat vascular issues such as aneurysms; however, once the stents are manufactured the porosity is fixed. The following embodiments describe an insert that is used with a stent to effectively decrease the porosity of a stent, as well as stents that utilize such an insert.

Figure 21:
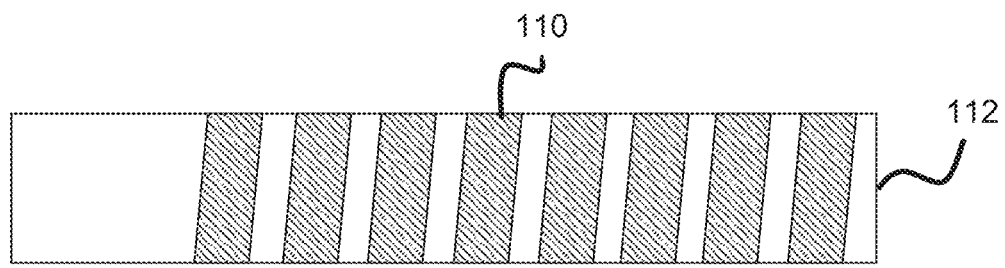
FIG. 21 illustrates an insert that can be used with a stent.

FIG. 21 illustrates a film 110 used as a stent insert. The film 110 can be wrapped around a cylinder or mandrel 112, which approximates the stent diameter, in order to create a helical or spiral shape. The film may be polymeric, e.g. PTFE, and may have a completely customizable porosity depending on the properties of the film. The film porosity can be controlled by including pores of various sizes on the film, or can be controlled by the material properties or thickness of the film, or via a combination of these factors. Alternatively the film may be a metallic mesh or a fabric material.

Figure 22:
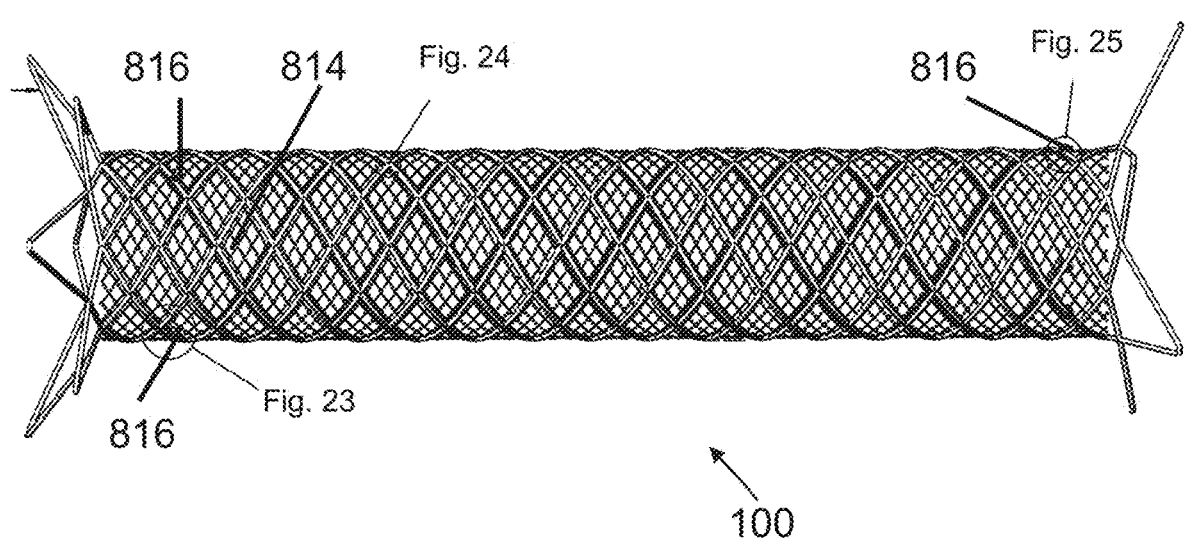
FIGS. 22-27 illustrate a dual layer stent.

FIG. 22 shows a dual layer stent 100 comprising an inner layer formed of one or more wires 204, and an outer layer formed of one or more wires 102. In certain embodiments the outer layer comprises one wire 102 which may wind back and forth along the length of the outer layer. For example, the outer layer may comprise one wire 102 that loops back to create a pattern that travels in two directions across the length of the stent. In another example the outer layer comprises more than one wire 102.

Figure 23:
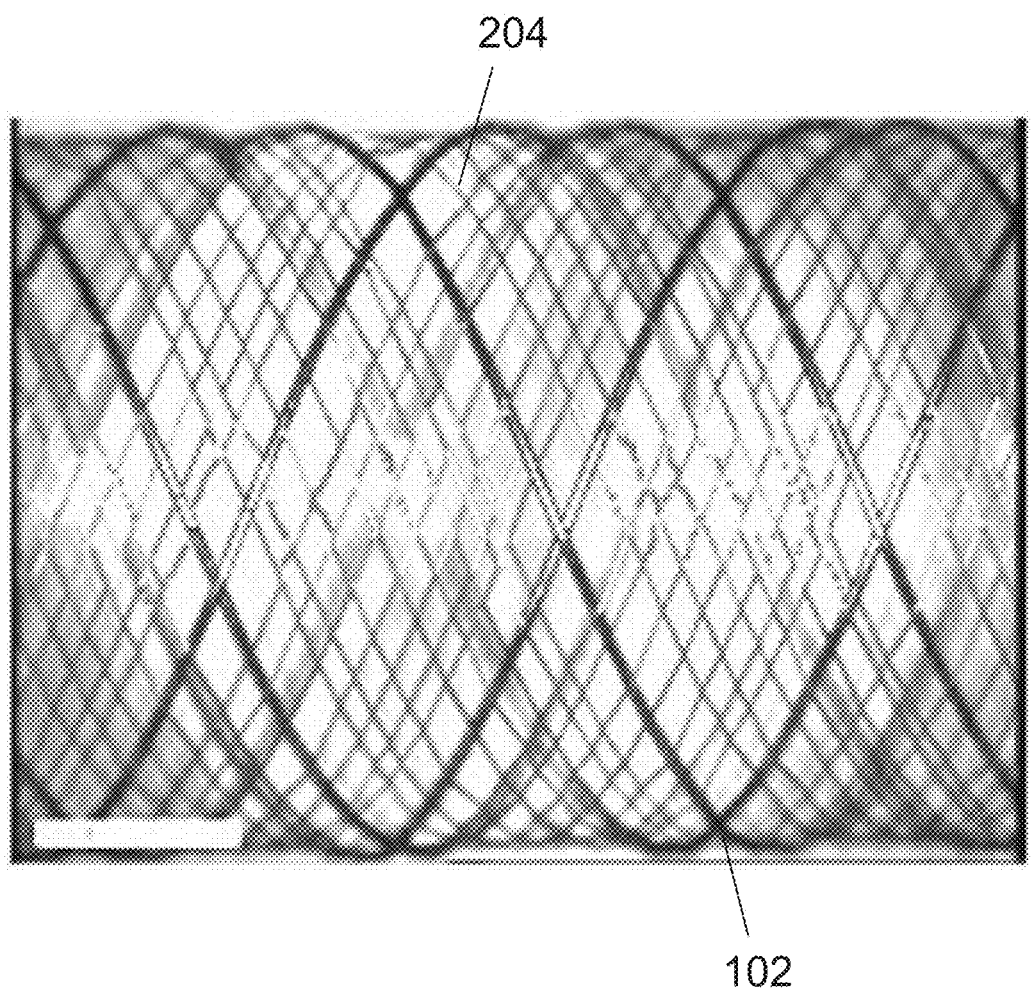
Figure 24:
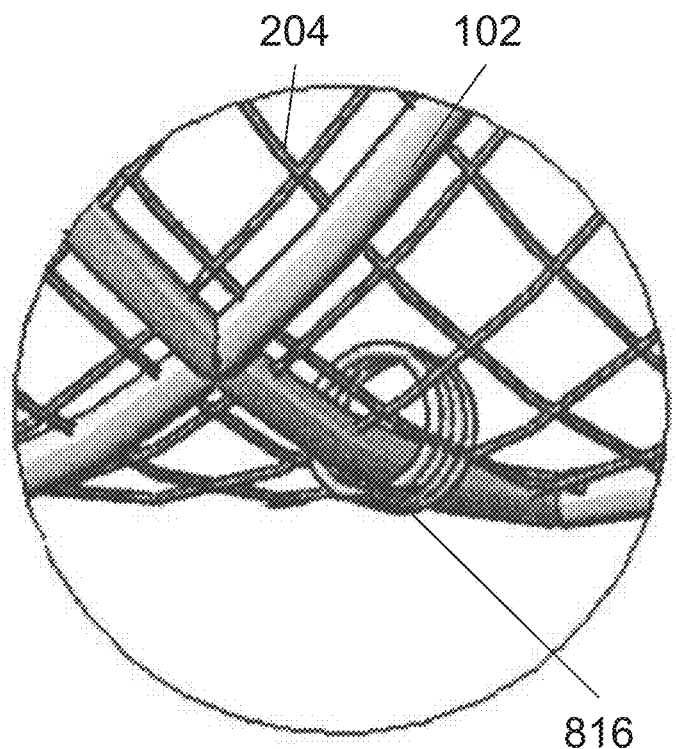
Figure 25:
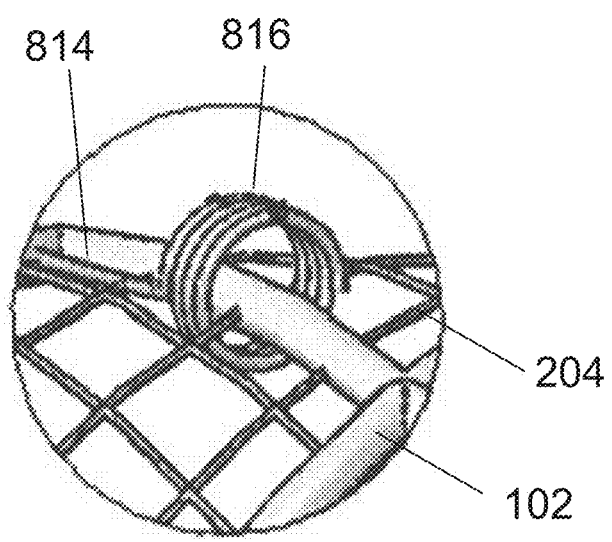
Figure 26:
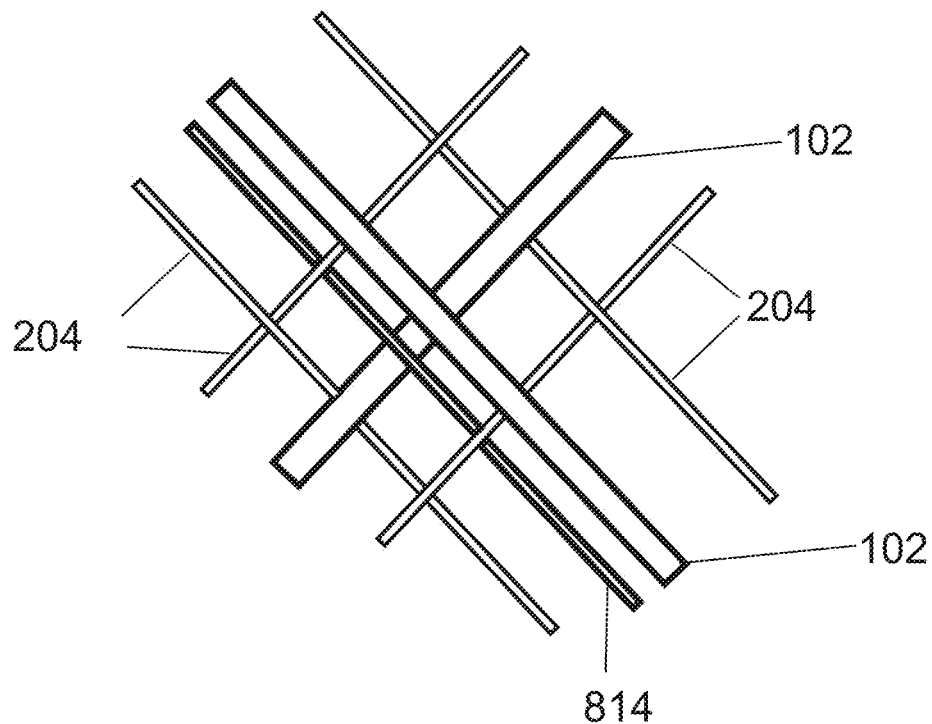

FIG. 23 shows a magnified view of a portion of the stent 100 shown in FIG. 2. Stent 100 may employ one or more support wires 814 that are positioned alongside or parallel to a wire 102 and may alternately proceed above outer layer wires 102 and below inner layer wires 204 to thereby connect the inner and outer layers, as shown in FIG. 26. One or more windings 816 may be formed by the support wires 814 about the wire 102 at various locations along a length of the wire 102, e.g. at a proximal portion and/or a distal portion of the stent and/or at beginning and end points of the support wire 814, as shown in FIGS. 4-5. Windings 816 may also be formed at one or more locations along the length of the wire 814 between the proximal and distal ends of wire 814.

Multiple support wires 814 may be used along the length of the stent, e.g. support wires can start from different points along wires 102 or along different constituent wire elements 102 which make up the outer layer. In certain embodiments, the support wires 814 that parallel certain wires 102 and that are anchored to the same wires 102 by the windings 816 of the wire 814 function as physical boundaries within which pockets or sleeves are formed between the inner and outer layers of the stent 100. Within these pockets, one or more films 110 may be positioned or secured.

Figure 27:
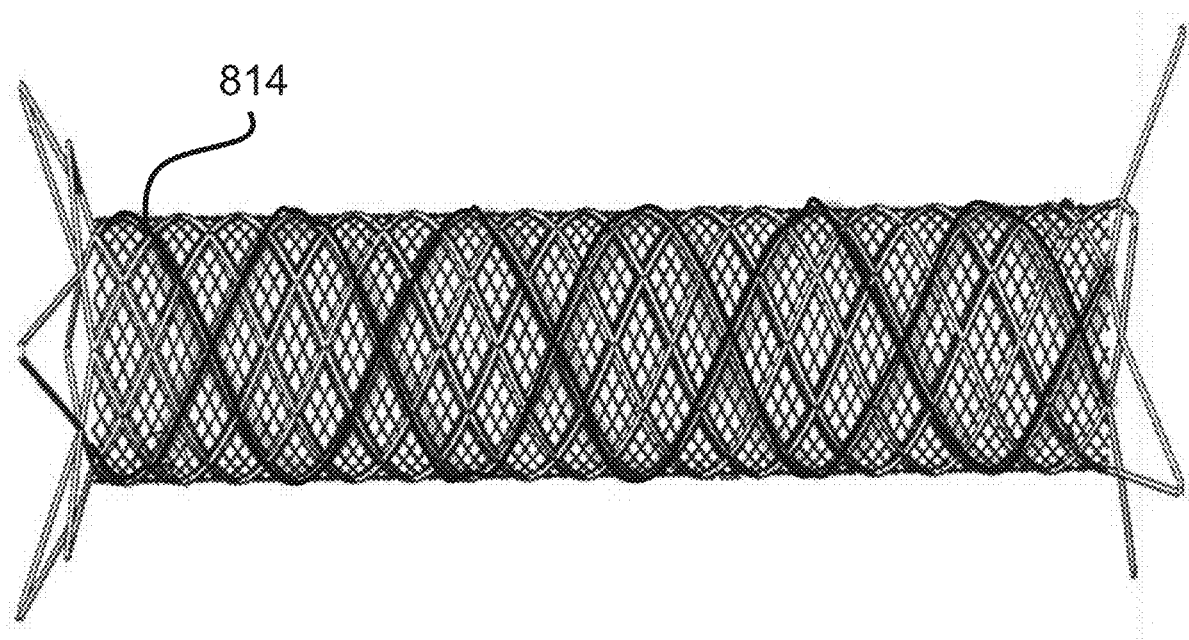

FIG. 27 illustrates a dual layer stent with two support wires 814 shown in shading in FIG. 27. Each support wire 814 parallels a different wire 102 or different length of the same wire 102. Support wires 814 create pockets between the inner and outer layers of the stent within which the film may sit and be secured.

Figure 28:
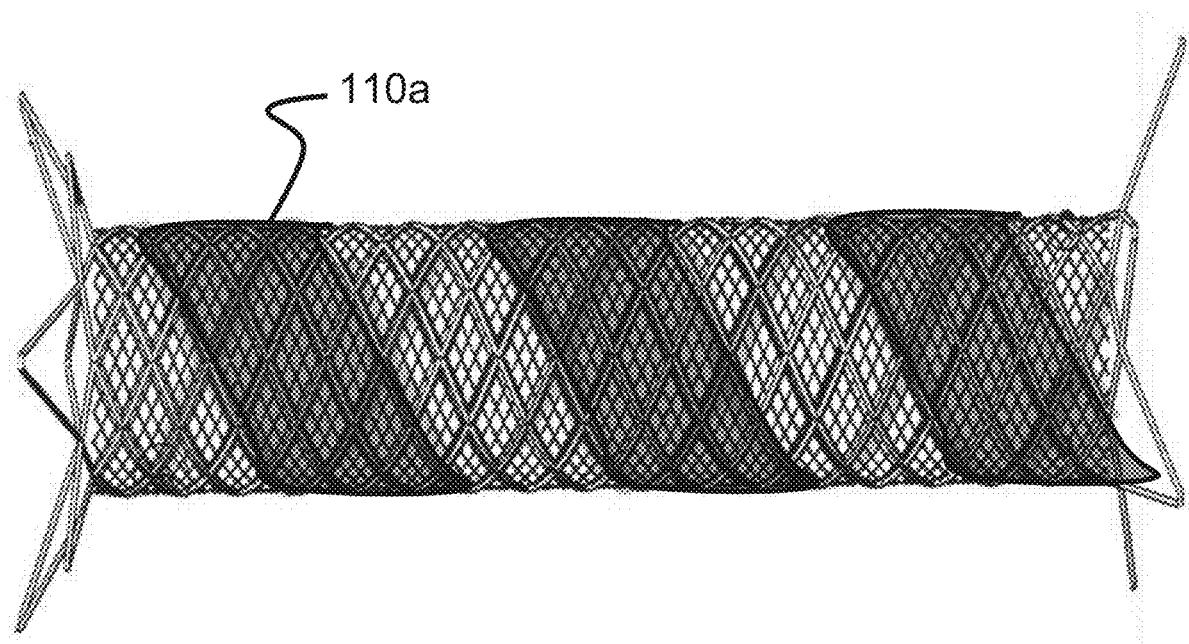
FIGS. 28-32 illustrate a stent comprising one or more inserts.
Figure 29:
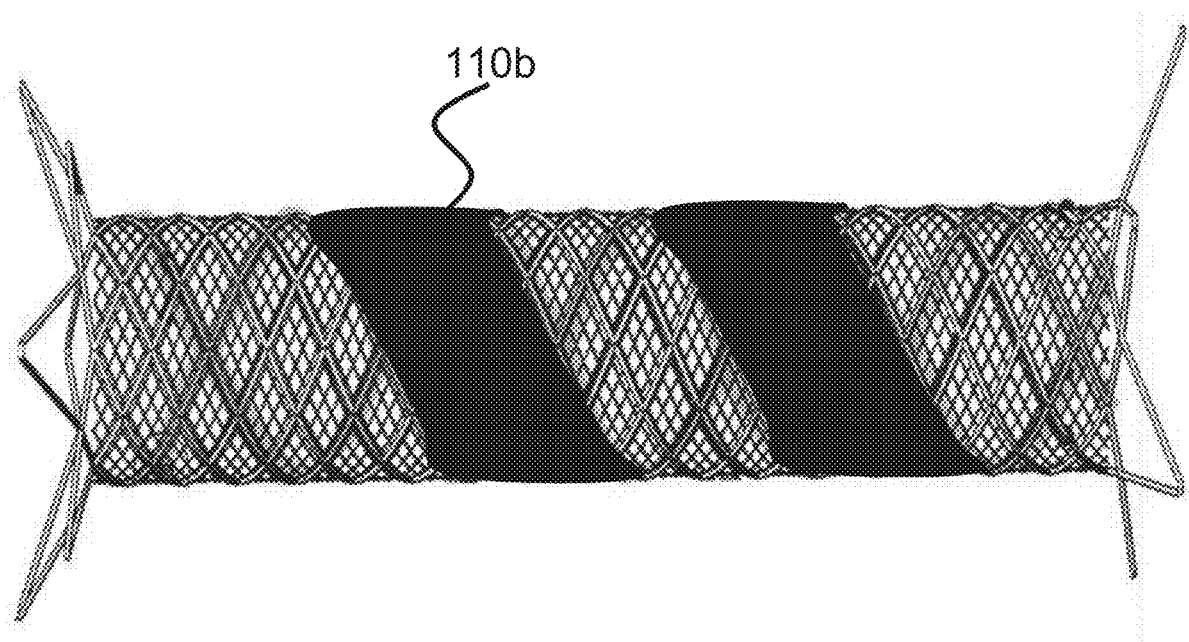
Figure 30:
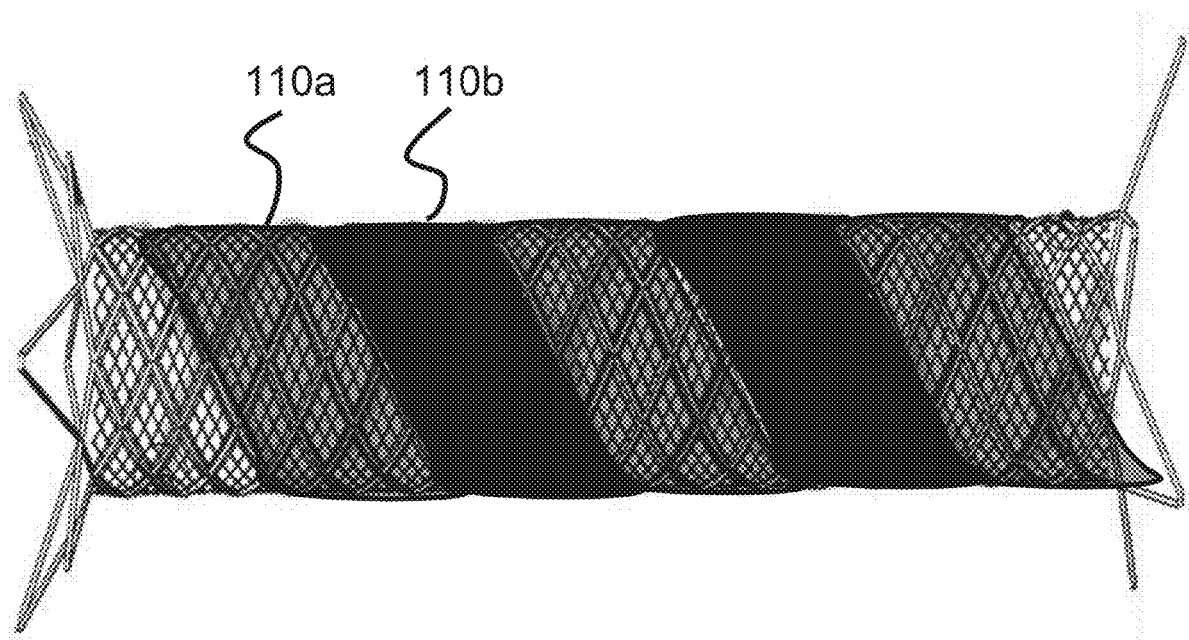
Figure 31:
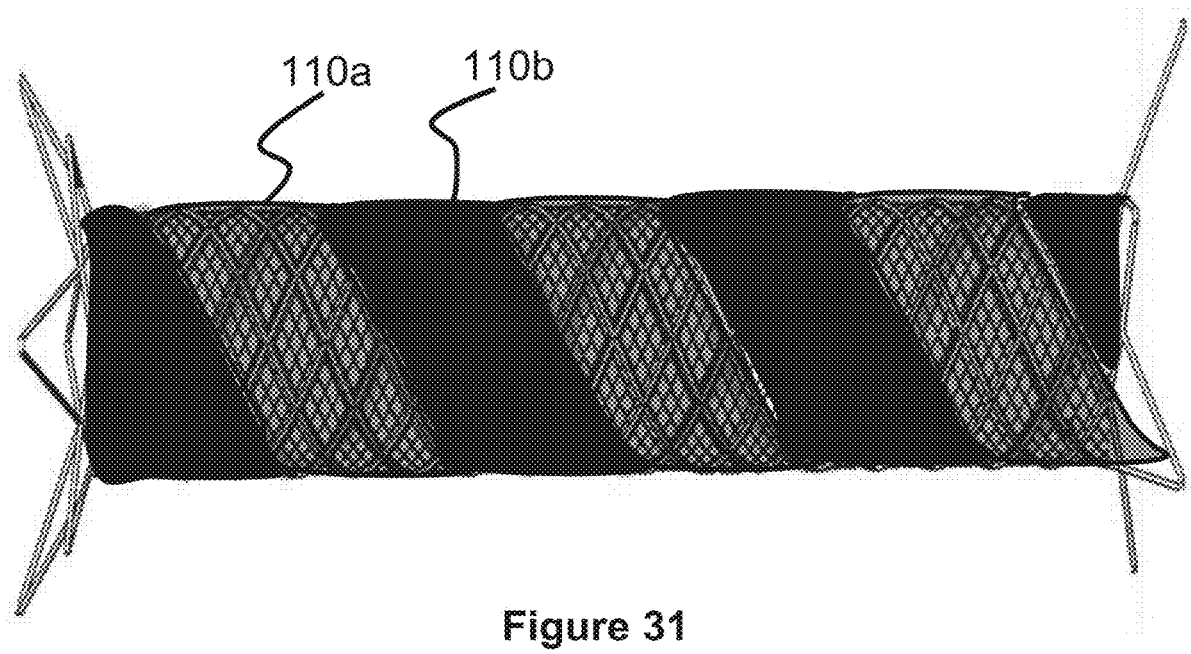
Figure 32:
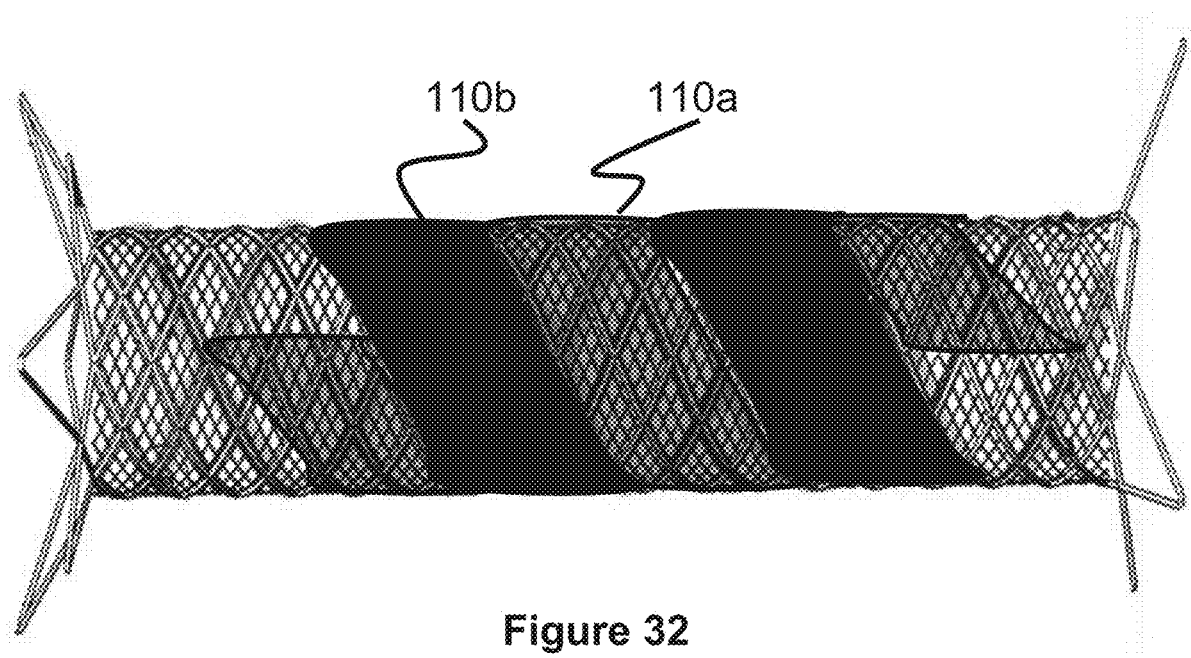

FIGS. 28-32 show various film configurations used with a stent. These figures are offered as examples are not meant to limit the possible film configurations. FIGS. 28-29 show two configurations in which a film 10a or 10b are located within different pockets between the inner and outer layers of the stent. FIGS. 30-32 illustrate various configurations where both films 110a and 110b sit. Though two films are shown, more films may also be used. The configuration utilizing multiple films can utilize films with different porosity to provide a variable porosity along the length of the stent. The film or films may span the entire length of the stent or just a portion of the stent.

In another embodiment the one or more inserts may be drug eluting.

In other embodiments a single layer stent, dual layer stent, or multiple (i.e. more than two) layer stent may utilize one or more inserts. It is contemplated that an insert could be located along the inner surface of the innermost stent layer (or along the inner surface of the single layer stent), between any of the layers, or on the outer surface of the outer layer (or the outer surface of the single layer stent). In embodiments in which the insert is located between two layers, it is contemplated that the insert could be connected to either adjacent layer or simply one of the adjacent layers. Any of such connection can be achieved via creation of a "pocket" as previously described, via mechanical ties or weaving, or via adhesive.

In other embodiments a single layer stent, dual layer stent, or multiple (i.e. more than two) layer stent may utilize a drug-eluting insert.

The inserts may be used on a single layer stent, dual layer stent, or stent with more than two layers. An example of a single layer stent is where a stent utilizes just one layer (i.e. one braid layer). For the single layer stent, the insert may be affixed to the inner or outer surface of the stent via adhesive, heat-treating, or other techniques. For the dual layer or other multiple layer (i.e. three or more layers) stents the inserts may sit on the inner surface, between layers of the stent, or on the outer surface of the stent via adhesive, heat treating, mechanical ties, or other techniques. Alternatively, inserts can sit on multiple surfaces of the stent in order to further augment the occlusive properties of the stent. In one example a dual-layer stent could include a film on the inner layer, and a film between the inner and outer layers. In another example the dual-layer stent could include a film between the inner and outer layers and a film on the outer layer. In another example a dual-layer stent could include a film on the inner layer and a film on the outer layer. In another example a dual-layer stent could include a film on the inner and outer layers, as well as between the inner and outer layers.

While the insert has been described in one embodiment as having a helical or spiral shape, other shapes are possible. For example, the insert could be made up of a plurality of elongated insert members that are woven or otherwise connected between one or more stent layers. In another example, the insert may have a tubular shape, allowing it to be located on the outer surface, inner surface, or between layers of a stent.

While a braided stent has been described, it should be understood that other types of stents are possible. For example, a stent may be formed from a laser-cut tube or sheet, or a non-braided polymer-based stent.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A stent comprising:
    an outer layer formed from one or more braided wires;
    an inner layer formed from one or more braided wires;
    one or more support wires woven through said outer layer and through said inner layer so as to create a first pocket; and,
    a first film contained within said first pocket.

2. The stent of claim 1, wherein said one or more support wires comprise two support wires arranged helically along said stent.

3. The stent of claim 2, wherein said first pocket has a helical shape.

4. The stent of claim 3, wherein said first film has a helical shape.

5. The stent of claim 1, wherein said one or more support wires create said first pocket and a second pocket.

6. The stent of claim 5, further comprising a second film contained in said second pocket.

7. The stent of claim 6, wherein said first film and said second film have a helical shape.

8. The stent of claim 7, wherein said first film and said second film have different porosities relative to each other.

9. The stent of claim 1, wherein said first film is composed of PTFE.

10. The stent of claim 1, wherein said first film is a metallic mesh.

11. The stent of claim 1, wherein said first film is a fabric.

12. The stent of claim 1, wherein said one or more support wires extends parallel to a wire from said one or more braided wires of said outer layer.

13. The stent of claim 1, wherein said first pocket has edges defining both a length and a width.

14. A stent comprising:
    an outer braided layer forming a tubular shape;
    an inner braided layer forming a tubular shape and being fixed within said outer braided layer;
    one or more support wires woven through said outer braided layer and through said inner braided layer so as to create a first sleeve; and,
    a first film contained within said first sleeve.

15. The stent of claim 14, wherein said one or more support wires comprise two support wires arranged helically along said stent.

16. The stent of claim 15, wherein said first film has a helical shape.

17. The stent of claim 14, wherein said first sleeve has a helical shape.

18. The stent of claim 14, wherein said one or more support wires create said first pocket and a second pocket.

19. The stent of claim 14, wherein said first sleeve has edges defining both a length and a width.

20. A stent having a tubular shape formed from two braided layers that are connected to each other to form a sleeve extending around at least a portion of said tubular shape; said sleeve containing a film.

21. The stent of claim 20, wherein said sleeve extends helically along a length of said tubular shape.

22. The stent of claim 21, wherein said two braided layers are connected by at least one interwoven support wire that defines a shape of said sleeve.

* * * * *